US012637707B2

(12) United States Patent (10) Patent No.: US 12,637,707 B2
Wu et al. (45) Date of Patent: May 26, 2026

(54) METHODS, COMPOSITIONS AND KITS TO IMPROVE SEEDING EFFICIENCY OF FLOW CELLS WITH POLYNUCLEOTIDES

(71) Applicants: Illumina, Inc., San Diego, CA (US); Illumina Cambridge Limited, Cambridge (GB)

(72) Inventors: Yir-Shyuan Wu, San Diego, CA (US); Filiz Gorpe-Yasar, San Diego, CA (US); Tarun Kumar Khurana, San Diego, CA (US); Jonathan Mark Boutell, Cambridge (GB)

(73) Assignees: Illumina, Inc., San Diego, CA (US); Illumina Cambridge Limited (GB)

( * ) Notice: Subject to any disclaimer, the term of this patent is extended or adjusted under 35 U.S.C. 154(b) by 433 days.

(21) Appl. No.: 18/274,974

(22) PCT Filed: Jan. 28, 2022

(86) PCT No.: PCT/US2022/014329
§ 371 (c)(1),
(2) Date: Jul. 28, 2023

(87) PCT Pub. No.: WO2022/165188
PCT Pub. Date: Aug. 4, 2022

(65) Prior Publication Data
US 2024/0117416 A1 Apr. 11, 2024

Related U.S. Application Data

(60) Provisional application No. 63/143,680, filed on Jan. 29, 2021.

(51) Int. Cl.
*C12Q 1/6834* (2018.01)
*C12Q 1/6844* (2018.01)
*C12Q 1/6874* (2018.01)

(52) U.S. Cl.
CPC ......... *C12Q 1/6834* (2013.01); *C12Q 1/6844* (2013.01); *C12Q 1/6874* (2013.01)

(58) Field of Classification Search
None
See application file for complete search history.

(56) References Cited

U.S. PATENT DOCUMENTS

| | | | | |
|---|---|---|---|---|
| 9,334,531 B2 * | 5/2016 | Li | | C12Q 1/686 |
| 2013/0338042 A1 * | 12/2013 | Shen | | C12Q 1/6874 |
| | | | | 506/26 |
| 2017/0137876 A1 * | 5/2017 | Rigatti | | C12Q 1/6844 |

FOREIGN PATENT DOCUMENTS

| | | |
|---|---|---|
| JP | 2015-519084 A | 7/2015 |
| JP | 2016-508715 A | 3/2016 |
| WO | 2013/188582 A1 | 12/2013 |

(Continued)

OTHER PUBLICATIONS

Lindner, Nora; International Preliminary Report on Patentability and Written Opinion; The International Bureau of WIPO, PCT/US2022/014329, Aug. 10, 2023.

(Continued)

*Primary Examiner* — Aaron A Priest
(74) *Attorney, Agent, or Firm* — Illumina, Inc.

(57) ABSTRACT

The disclosure relates to methods, compositions, and kits for improving seeding efficiency of flow cells with polynucleotides, and applications thereof, including for sequencing.

20 Claims, 7 Drawing Sheets

Specification includes a Sequence Listing.

(56) References Cited

FOREIGN PATENT DOCUMENTS

| WO | 2014/108810 | A2 | 7/2014 |
| WO | 2019/028047 | A1 | 2/2019 |
| WO | 2020/144373 | A1 | 7/2020 |

OTHER PUBLICATIONS

Hennard, Christophe; International Search Report and Written Opinion; European Patent Office, PCT/US2022/014329, May 12, 2022.
Tabata, Toshiyuki, Office Action, Japan Patent Office, Application No. 2023-545752, Feb. 3, 2026.

\* cited by examiner

Priming → Extension → Primer Invasion

Seeding & Amp.
on Surface ← Extension, Strand
Displacement & Release

Seed strand 4b    4a

A

B

AMS1
extension

C

Denature and re-
seed in shallow
liquid layer

D

Bridge
amplification

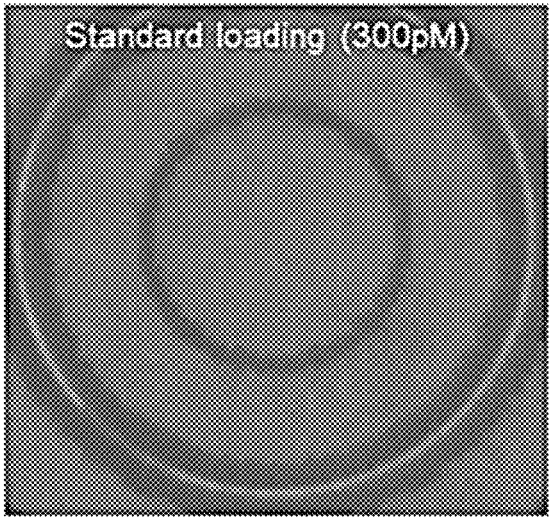
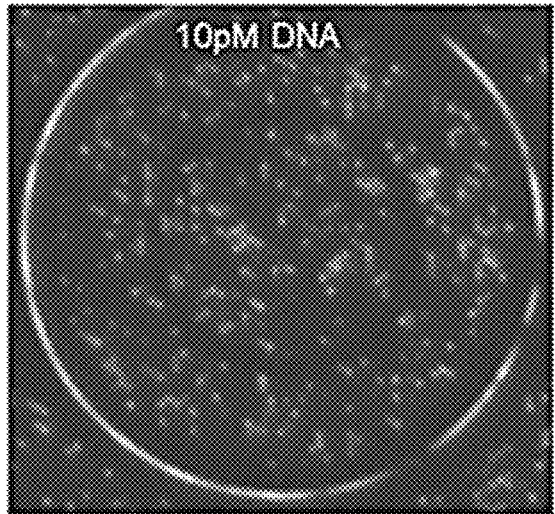
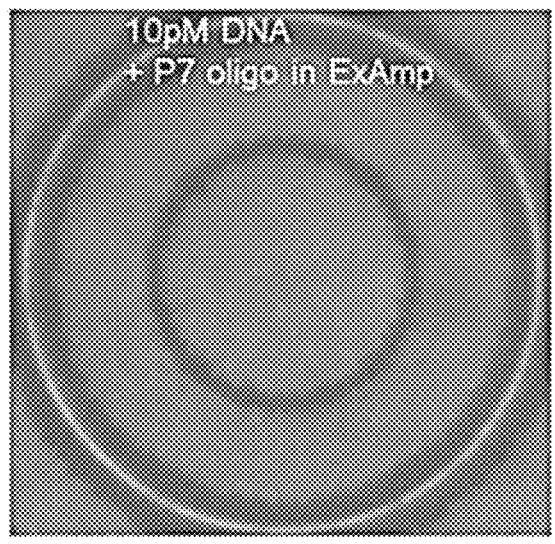
*FIG. 8*

METHODS, COMPOSITIONS AND KITS TO IMPROVE SEEDING EFFICIENCY OF FLOW CELLS WITH POLYNUCLEOTIDES

CROSS REFERENCE TO RELATED APPLICATIONS

This application is a U.S. National Stage Application filed under 35 U.S.C. § 371 and claims priority to International Application No: PCT/US2022/014329, filed on Jan. 28, 2022, which application claims priority to U.S. Provisional Application Ser. No. 63/143,680, filed on Jan. 29, 2021, the disclosures of which are incorporated herein by reference.

TECHNICAL FIELD

The disclosure relates to methods, compositions, and kits for improving seeding efficiency of flow cells with polynucleotides, and applications thereof, including for sequencing.

BACKGROUND

DNA sequencing is in a period of rapid change, in which capillary sequencing is no longer the technology of choice for most ultra-high-throughput applications. A new generation of instruments that utilize primed synthesis in flow cells to obtain, simultaneously, the sequence of millions of different DNA templates has changed the field.

Next-generation sequencing (NGS) platforms typically makes use of nucleic acid fragment libraries. Nucleic acid fragment libraries may be prepared using PCR-based methods or transposon-based methods. In the latter case, free transposon ends and a modified transposase are used to form a transposome complex. The transposome complex is then used to fragment and tag nucleic acids, generating a sequencer-ready tagmented library. The transposome complex can be formed in solution or affix to a solid support, like beads. In order to use transposome complexes that are bound to solid support (e.g., transposome beads) in flow cells, the nucleic acid components of the transposome complexes must be released and then seeded onto a flow cell surface. Typically, the means to do so is by the use of heat, or a competitive binding agent used in excess (e.g., biotin). Heat, however, leads to increased diffusion in the flow cell, which will disrupt the spatial co-location of the clusters formed.

SUMMARY

The disclosure provides compositions, methods and kit that address the problem of low seeding efficiency of flow cells. In particular, the composition, methods and kits of the disclosure provide for the release of amplified nucleic acids from beads to seed flow cells by using exclusion amplification (ExAmp) to copy transposed polynucleotides on the beads with a primer in solution ("solution primer"). More specifically, strand invasion by use of the solution primer, leads to displacement of the copied strands into solution, thereby effectively releasing them from the beads and facilitating seeding of the flow cell. In additional embodiments, beads can further comprise bound amplification primer(s), in order to enhance the amplification and displacement of the amplified nucleic acids from the beads. In other embodiments, seeding efficiency of the flow cell can be improved or further improved by use of on-flow cell linear amplification and a shallow layer liquid denaturing/seeding work flow.

In a particular embodiment, the disclosure provides a method for seeding a flow cell with polynucleotide(s) released from a bead, comprising: (i) annealing a first primer to polynucleotide strands bound to a bead, wherein the 5' ends of the polynucleotide strands are bound to the bead using a first attachment agent, wherein the polynucleotide strands comprise adaptors that contain a sequence that is complementary to the sequence of the first primer, and wherein the first primer is in solution; (ii) extending from the first primer using a polymerase to form a double stranded polynucleotide product; (iii) carrying out primer invasion of the double stranded polynucleotide product by using additional amounts of the first primer and a recombinase; (iv) displacing and releasing from the bead a strand of the double stranded polynucleotide product of step (ii) by extending from the additional first primer in step (iii) using a polymerase; (v) seeding a flow cell by attaching the strand released in step (iv) to the surface of a flow cell using a second attachment agents; and optionally, repeating steps (iii) to (v) multiple times. In a further embodiment, the bead is generally spherical or generally ovoid in shape. In another embodiment, the bead has a diameter of about 500 nm, 1 µM, 1.1 µM, 1.2 µM, 1.3 µM, 1.4 µM, 1.5 µM, 1.6 µM, 1.7 µM, 1.8 µM, 1.9 µM, 2 µM, 2.1 µM, 2.2 µM, 2.3 µM, 2.4 µM, 2.5 µM, 2.6 µM, 2.7 µM, 2.8 µM, 2.9 µM, 3 µM, 3.1 µM, 3.2 µM, 3.3 µM, 3.4 µM, 3.5 µM, 3.6 µM, 3.7 µM, 3.8 µM, 3.9 µM, 4 µM, 4.1 µM, 4.2 µM, 4.3 µM, 4.4 µM, 4.5 µM, 4.6 µM, 4.7 µM, 4.8 µM, 4.9 µM, 5.0 µM, 5.1 µM, 5.2 µM, 5.3 µM, 5.4 µM, 5.5 µM, 5.6 µM, 5.7 µM, 5.8 µM, 5.9 µM, 6 µM, 6.1 µM, 6.2 µM, 6.3 µM, 6.4 µM, 6.5 µM, 6.6 µM, 6.7 µM, 6.8 µM, 6.9 µM, 7 µM, 7.1 µM, 7.2 µM, 7.3 µM, 7.4 µM, 7.5 µM, 7.6 µM, 7.7 µM, 7.8 µM, 7.9 µM, 8 µM, 8.1 µM, 8.2 µM, 8.3 µM, 8.4 µM, 8.5 µM, 8.6 µM, 8.7 µM, 8.8 µM, 8.9 µM, 9.0 µM, 9.1 µM, 9.2 µM, 9.3 µM, 9.4 µM, 9.5 µM, 9.6 µM, 9.7 µM, 9.8 µM, 9.9 µM, 10 µM, or a range that includes or is in between any two of foregoing distances. In yet another embodiment, the bead has a diameter of about 500 nm, 1 µM, 1.1 µM, 1.2 µM, 1.3 µM, 1.4 µM, 1.5 µM, 1.6 µM, 1.7 µM, 1.8 µM, 1.9 µM, 2 µM, 2.1 µM, 2.2 µM, 2.3 µM, 2.4 µM, 2.5 µM, 2.6 µM, 2.7 µM, 2.8 µM, 2.9 µM, 3 µM, 3.1 µM, 3.2 µM, 3.3 µM, 3.4 µM, 3.5 µM, or a range that includes or is in between any two of foregoing distances. In a certain embodiment, the bead is comprised of a polymeric material, a silica material, a zirconia material, or a superparamagnetic material. In a further embodiment, the bead is comprised of a superparamagnetic material. In yet a further embodiment, the bead is functionalized with a coating or layer selected from biotin; streptavidin; amine groups; carboxyl groups; epoxy groups; tosyl groups; an antibody or an antigen; a polyhistidine tag or a carrier comprising a metal ion; and a receptor or a ligand. In a particular embodiment, the beads are not immobilized on one or more surfaces of the flow cell. In an alternate embodiment, the beads are immobilized on one or more surfaces of the flow cell using an attachment agent. In another embodiment, the attachment agent is a biotin/streptavidin linkage or base pairing between two complementary sequences. In yet another embodiment, the polynucleotide strands bound to the bead comprise genomic DNA. In a further embodiment, the polynucleotide strands bound to the bead comprise long template DNA. In yet a further embodiment, the polynucleotide strands bound to the bead comprise DNA from a subject's sample. In a certain embodiment, the subject's sample is a urine, blood, saliva, tissue, serum, plasma, sputum, bile, fecal, hair, skin, and/or primary cell sample. In another embodiment, the polynucleotide strands are tagmented and bound to the bead by use of a transposome linked to the beads. In yet another embodiment, the transposome linked to the beads comprises transposase Tn5, or a mutant or variant thereof. In a further embodiment, the polynucleotide strands comprise a first portion of sequence that was bound to bead by first attachment agents and a second portion of sequence that was tagmented and ligated to the first portion of sequence by use of a transposomes linked to the bead and a ligase. In yet a further embodiment, the transposome linked to the beads comprises transposase Tn5, or a mutant or variant thereof. In another embodiment, the first portion of the sequence comprises one or more barcode or index sequences, one or more universal primer sequences, and/or a mosaic end sequence. In yet another embodiment, the first portion of the sequence comprises one or more barcode or index sequences, one or more universal primer sequences, and a mosaic end sequence, and wherein the mosaic end sequence is located at the 3' end of the first portion of the sequence. In a certain embodiment, the adaptors comprise a first sequence that is complementary and can hybridize with the first portion of the sequence of the polynucleotide strands, and wherein the adaptors comprise a second sequence that is not complementary and cannot hybridize with the first portion of the sequence of the polynucleotide strands. In another embodiment, the second sequence of the adaptors comprises a sequence that is complementary to the sequence of the first primer. In yet another embodiment, the second portion of sequence of the polynucleotide strands comprises gDNA. In a certain embodiment, the second portion of sequence of the polynucleotide strands comprise long template DNA. In a further embodiment, the second portion of sequence of the polynucleotide strands comprise DNA from a subject's sample.

In yet a further embodiment, the subject's sample is a urine, blood, saliva, tissue, serum, plasma, sputum, bile, fecal, hair, skin, and/or primary cell sample. In a certain embodiment, the first attachment agent and second attachment agent are selected from a biotin/streptavidin linkage, a covalent bond, base pairing between two complementary sequences, an antibody binding an antigen, an antibody binding another antibody, a polyhistidine tag binding a carrier comprising a metal ion, and a receptor binding a ligand. In another embodiment, the first attachment agent is a biotin/streptavidin or avidin linkage, and wherein the second attachment agent is base pairing between two complementary sequences. In yet another embodiment, the polynucleotide strands comprise biotin residues at the 5' ends, and the bead comprises streptavidin residues. In a further embodiment, the first primer has the sequence of SEQ ID NO:1 or SEQ ID NO:2. In yet a further embodiment, the first primer has the sequence of SEQ ID NO: 2. In a certain embodiment, a DNA polymerase is used to extend the sequence from the first primer. In a further embodiment, the method provides for linear copying of the polynucleotide strands. In a certain embodiment, the flow cell is a patterned flow cell. In a further embodiment, the strands released from the beads are bound by capture agents on the flow cell surface. In yet a further embodiment, the capture agents are located on an array of features of patterned flow cell, wherein the capture agents are not located on interstitial regions between the features. In another embodiment, the array of features of patterned flow cell are wells. In yet another embodiment, the capture agents are capture nucleic acids bound to the surface of the flow cell, and wherein the strands release from the beads comprise sequences that can hybridize with the primers bound to the surface of the flow cell. In a further embodiment, the capture nucleic acids comprise a universal capture sequence. In yet a further embodiment, the universal capture sequence comprises P5 5'-AATGATACGGCGACCACCGA-3' ((SEQ ID NO: 1)) or P7 (5'-CAAGCAGAAGACGGCATACGA-3' (SEQ ID NO: 2)), or fragments thereof. In an alternate embodiment, the universal capture sequence comprises anti-P5: 5'-TCGGTGGTCGCCGTATCATT-3' (SEQ ID NO: 3) or anti-P7: 5'-TCGTATGCCGTCTTCTGCTTG-3' (SEQ ID NO: 4)), or fragments thereof. In a further embodiment, the capture nucleic acids further comprise a sequencing primer binding site (SBS), a target-specific capture region, a restriction site, and/or a linker region. In yet a further embodiment, the SBS is SBS3: 5'-ACACTCTTTCCCTACACGACGCTCTTCCG ATCT-3' (SEQ ID NO: 5) or SBS8: 5'-CGGTCTCGGCAT-TCCTGCTGAACCGC TCTTCCGATCT-3' (SEQ ID NO: 6). In a certain embodiment, the method further comprises: performing an on-flow cell linear amplification reaction to make a copy of the polynucleotides seeded on the flow cell surface; and denaturing and seeding the copied polynucleotides on the flow cell surface. In a further embodiment, the on-flow cell linear amplification reaction comprises a low temperature AMS1 first extension reaction. In yet a further embodiment, the copied polynucleotides are denatured by use of a hybridization buffer comprising a chemical denaturant. In another embodiment, the chemical denaturant is formamide. In yet another embodiment, the mixture comprises HT1. In a further embodiment, the hybridization buffer comprising a chemical denaturant shallowly covers the surface of the patterned flow cell so that the array features on the patterned flow cell surface are in fluid contact with each other. In yet a further embodiment, the method further comprises: forming clusters on the surface of the patterned flow cell by using bridge amplification to make a plurality of copies of each seeded polynucleotide. In yet another embodiment, the method further comprises: sequencing by synthesis the clusters generated on the surface of the patterned flow cell.

In a particular embodiment, a method for seeding a flow cell with polynucleotide(s) released from a bead, comprising: (i) providing a bead that comprises polynucleotide strands bound to a bead, wherein the 5' ends of the polynucleotide strands are bound to the bead using a first attachment agent and wherein the polynucleotide strands comprise adaptors that contain a sequence that is complementary to the sequence of a first primer, and wherein the bead also comprises a bound first amplification primer, wherein the first amplification primer is bound to the bead by a third attachment agent, wherein the first amplification primer has a sequence that is different and not complementary to the sequence of the first primer, and wherein the polynucleotide strands contain a sequence that is complementary to the first amplification primer; (ii) annealing the first primer to the polynucleotide strands bound to a bead, wherein the first primer is in solution; (iii) extending from the first primer using a polymerase to form a double stranded polynucleotide product; (iv) carrying out primer invasion of the double stranded polynucleotide product by using additional amounts of the first primer and/or the first amplification primer and a recombinase; (v) displacing and releasing from the bead a strand of the double stranded polynucleotide product of step (iii) by extending from the additional first primer and/or the first amplification primer in step (iv) with a polymerase; (vi) seeding a flow cell by attaching the strand released in step (v) to the surface of a flow cell using a second attachment agent; and optionally, repeating steps (ii) to (vi) multiple times. In another embodiment, the disclosure provides a method for seeding a flow cell with polynucleotide(s) released from a bead, comprising: (i) providing a bead that comprises polynucleotide strands bound to a bead, wherein the 5' ends of the polynucleotide strands are bound to the bead using a biotin/streptavidin linkage, and wherein the bead also comprises a bound second amplification primer, wherein the second amplification primer is bound to the bead by a third attachment agent, wherein the second amplification primer has a sequence that is different and not complementary to the sequence of a second primer, and wherein the polynucleotide strands contain a sequence that is complementary to the second amplification primer and contains a sequence that is complementary to the second primer; (ii) annealing the second amplification primer to the polynucleotide strands bound to a bead; (iii) extending from the second amplification primer using a polymerase to form a double stranded polynucleotide product; then step (a), or step (b) and (b'): (a) introducing the bead into a flow cell and using heat and excess biotin to release the double stranded polynucleotide product as single stranded polynucleotide products from the bead; or (b) carrying out primer invasion of the double stranded polynucleotide product by using the second primer and a recombinase, wherein the second primer is in solution; (b') displacing and releasing from the bead a strand of the double stranded polynucleotide product by extending from the second primer with a polymerase; and (iv) seeding the surface of a flow cell using a second attachment agent with the single stranded polynucleotide product(s) released in step (a) or the strand of the double stranded polynucleotide product released from the bead in step (b'); and optionally, repeating steps (ii) to (iv) multiple times. In a further embodiment the bead is immobilized to the surface(s) of the flow cell using an attachment agent. In yet a further embodiment, the attachment agent is selected from a biotin/streptavidin linkage, a covalent bond, base pairing between two complementary sequences, an antibody binding an antigen, an antibody binding another antibody, a polyhistidine tag binding a carrier comprising a metal ion, and a receptor binding a ligand. In yet a further embodiment, the attachment agent is a biotin/streptavidin linkage or base pairing between two complementary sequences. In an alternate embodiment, the bead is not immobilized to the surface(s) of the flow cell using an attachment agent. In a certain embodiment, the flow cell is a patterned flow cell. In a further embodiment, the strands released from the beads are bound by capture agents on the flow cell surface. In yet a further embodiment, the capture agents are located on an array of features of patterned flow cell, wherein the capture agents are not located on interstitial regions between the features. In another embodiment, the array of features of patterned flow cell are wells. In yet another embodiment, the capture agents are capture nucleic acids bound to the surface of the flow cell, and wherein the strands release from the beads comprise sequences that can hybridize with the primers bound to the surface of the flow cell. In a further embodiment, the capture nucleic acids comprise a universal capture sequence. In yet a further embodiment, the universal capture sequence comprises P5 5'-AATGATACGGCGAC-CACCGA-3' ((SEQ ID NO: 1)) or P7 (5'-CAAGCAGAA-GACGGCATACGA-3' (SEQ ID NO: 2)), or fragments thereof. In an alternate embodiment, the universal capture sequence comprises anti-P5: 5'-TCGGTGGTCGCCGTAT-CATT-3' (SEQ ID NO: 3) or anti-P7: 5'-TCGTATGCCGTCTTCTGCTTG-3' (SEQ ID NO: 4)), or fragments thereof. In a further embodiment, the capture nucleic acids further comprise a sequencing primer binding site (SBS), a target-specific capture region, a restriction site, and/or a linker region. In yet a further embodiment, the SBS is SBS3: 5'-ACACTCTTTCCCTACACGACGCTCTTCCG ATCT-3' (SEQ ID NO: 5) or SBS8: 5'-CGGTCTCGGCAT-TCCTGCTGAACCGC TCTTCCGATCT-3' (SEQ ID NO: 6). In a certain embodiment, the method further comprises: performing an on-flow cell linear amplification reaction to make a copy of the polynucleotides seeded on the flow cell surface; and denaturing and seeding the copied polynucleotides on the flow cell surface. In a further embodiment, the on-flow cell linear amplification reaction comprises a low temperature AMS1 first extension reaction. In yet a further embodiment, the copied polynucleotides are denatured by use of a hybridization buffer comprising a chemical denaturant. In another embodiment, the chemical denaturant is formamide. In yet another embodiment, the hybridization buffer comprises HT1. In a further embodiment, the hybridization buffer comprising a chemical denaturant shallowly covers the surface of the patterned flow cell so that the array features on the patterned flow cell surface are in fluid contact with each other. In yet a further embodiment, the method further comprises: forming clusters on the surface of the patterned flow cell by using bridge amplification to make a plurality of copies of each seeded polynucleotide. In yet another embodiment, the method further comprises: sequencing by synthesis the clusters generated on the surface of the patterned flow cell.

In a certain embodiment, the disclosure further provides a method for seeding a flow cell with polynucleotide(s) released from a bead, comprising: (i) providing a bead that comprises polynucleotide strands bound to a bead, wherein the 5' ends of the polynucleotide strands are bound to the bead using a biotin/streptavidin linkage, and wherein the bead also comprises a bound first and second amplification primer, wherein the first and second amplification primer is bound to the bead by an attachment agent, wherein the first amplification primer has a sequence that is at least 99% identical to the sequence of a first primer, wherein the second amplification primer has a sequence that is at least 99% identical to the sequence of a second primer, and wherein the polynucleotide strands contain a sequence that is complementary to the first amplification primer, and contains a sequence that is complimentary to the second amplification primer; (ii) annealing the first and second amplification primers to the polynucleotide strands bound to a bead; (iii) extending from the first and second amplification primers using a polymerase to form a clustering of a double stranded polynucleotide products; then either step (A), or step (B) and (B'): (A) introducing the bead into a flow cell and using heat and excess biotin to release the double stranded polynucleotide product as single stranded polynucleotide products from the bead; or (B) carrying out primer invasion of the double stranded polynucleotide product by using the first primer and/or the second primer and a recombinase, wherein the first and second primer is in solution; and (B') displacing and releasing from the bead a strand of the double stranded polynucleotide product by extending from the first and/or second primer with a polymerase; and (iv) seeding the surface of a flow cell using an attachment agent with the single stranded polynucleotide product(s) released in step (A) or the strand of the double polynucleotide product released from bead in step (B'); and optionally, repeating steps (ii) to (iv) multiple times. In a further embodiment the bead is immobilized to the surface(s) of the flow cell using an attachment agent. In yet a further embodiment, the attachment agent is selected from a biotin/streptavidin linkage, a covalent bond, base pairing between two complementary sequences, an antibody binding an antigen, an antibody binding another antibody, a polyhistidine tag binding a carrier comprising a metal ion, and a receptor binding a ligand. In yet a further embodiment, the attachment agent is a biotin/streptavidin linkage or base pairing between two complementary sequences. In an alternate embodiment, the bead is not immobilized to the surface(s) of the flow cell using an attachment agent. In a certain embodiment, the flow cell is a patterned flow cell. In a further embodiment, the strands released from the beads are bound by capture agents on the flow cell surface. In yet a further embodiment, the capture agents are located on an array of features of patterned flow cell, wherein the capture agents are not located on interstitial regions between the features. In another embodiment, the array of features of patterned flow cell are wells. In yet another embodiment, the capture agents are capture nucleic acids bound to the surface of the flow cell, and wherein the strands release from the beads comprise sequences that can hybridize with the primers bound to the surface of the flow cell. In a further embodiment, the capture nucleic acids comprise a universal capture sequence. In yet a further embodiment, the universal capture sequence comprises P5 5'-AATGATACGGCGAC-CACCGA-3' ((SEQ ID NO: 1)) or P7 (5'-CAAGCAGAA-GACGGCATACGA-3' (SEQ ID NO: 2)), or fragments thereof. In an alternate embodiment, the universal capture sequence comprises anti-P5: 5'-TCGGTGGTCGCCGTAT-CATT-3' (SEQ ID NO: 3) or anti-P7: 5'-TCGTATGCCGTCTTCTGCTTG-3' (SEQ ID NO: 4)), or fragments thereof. In a further embodiment, the capture nucleic acids further comprise a sequencing primer binding site (SBS), a target-specific capture region, a restriction site, and/or a linker region. In yet a further embodiment, the SBS is SBS3: 5'-ACACTCTTTCCCTACACGACGCTCTTCCG ATCT-3' (SEQ ID NO: 5) or SBS8: 5'-CGGTCTCGGCAT-TCCTGCTGAACCGC TCTTCCGATCT-3' (SEQ ID NO: 6). In a certain embodiment, the method further comprises: performing an on-flow cell linear amplification reaction to make a copy of the polynucleotides seeded on the flow cell surface; and denaturing and seeding the copied polynucleotides on the flow cell surface. In a further embodiment, the on-flow cell linear amplification reaction comprises a low temperature AMS1 first extension reaction. In yet a further embodiment, the copied polynucleotides are denatured by use of a hybridization buffer comprising a chemical denaturant. In another embodiment, the chemical denaturant is formamide. In yet another embodiment, the hybridization buffer comprises HT1. In a further embodiment, the hybridization buffer comprising a chemical denaturant shallowly covers the surface of the patterned flow cell so that the array features on the patterned flow cell surface are in fluid contact with each other. In yet a further embodiment, the method further comprises: forming clusters on the surface of the patterned flow cell by using bridge amplification to make a plurality of copies of each seeded polynucleotide. In yet another embodiment, the method further comprises: sequencing by synthesis the clusters generated on the surface of the patterned flow cell.

In a certain embodiment, the disclosure also provides a method for increasing the seeding efficiency of polynucleotides on the surface of a flow cell, comprising: performing an on-flow cell linear amplification reaction to make a copy of the polynucleotides seeded on the flow cell surface; and denaturing and seeding the copied polynucleotides on the flow cell surface. In a further embodiment, the on-flow cell linear amplification reaction comprises a low temperature AMS1 first extension reaction. In yet a further embodiment, the copied polynucleotides are denatured by use of a hybridization solution comprising a chemical denaturant. In another embodiment, the chemical denaturant is formamide.

In yet another embodiment, the hybridization solution comprises HT1. In a further embodiment, the mixture shallowly covers the surface of the patterned flow cell so that the array features on the patterned flow cell surface are in fluid contact with each other. In yet a further embodiment, the method further comprises: forming clusters on the surface of the patterned flow cell by using bridge amplification to make a plurality of copies of each seeded polynucleotide. In another embodiment, the method further comprises: sequencing by synthesis the clusters generated on the surface of the patterned flow cell.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 6A-D shows the work flow for on-flow cell linear amplification: (A) polynucleotides of a DNA library are seeded in a well of a flow cell. (B) 1st extension with Illumina™ AMS1 results in double stranded DNA (one copied anchor strand with original strand). (C) After shallow layer liquid denaturing/seeding, a strand exits the original well and seeds nearby wells. (D) After bridge amplification, there is a higher chance to collect the sequencing info from the DNA libraries.

FIG. 8 provides photos of the bottom wells of a patterned flow cell to evaluate whether the flow cell can be seeded with a minimal amount DNA using a method disclosed herein. Top photo: picture of the bottom of flow cell which has been loaded with the standard amount (300 μM) of DNA. Middle photo: picture of the bottom of flow cell which has been loaded with 10 μM of DNA. Bottom photo:

picture of the bottom of flow cell which has been loaded with 10 μM of DNA and P7 oligonucleotides and ExAmp. The photos indicate that the wells of patterned flowcells can be fully occupied with starting low amounts of DNA (i.e., 10 μM) when using the amplification process described herein.

Figure 9:
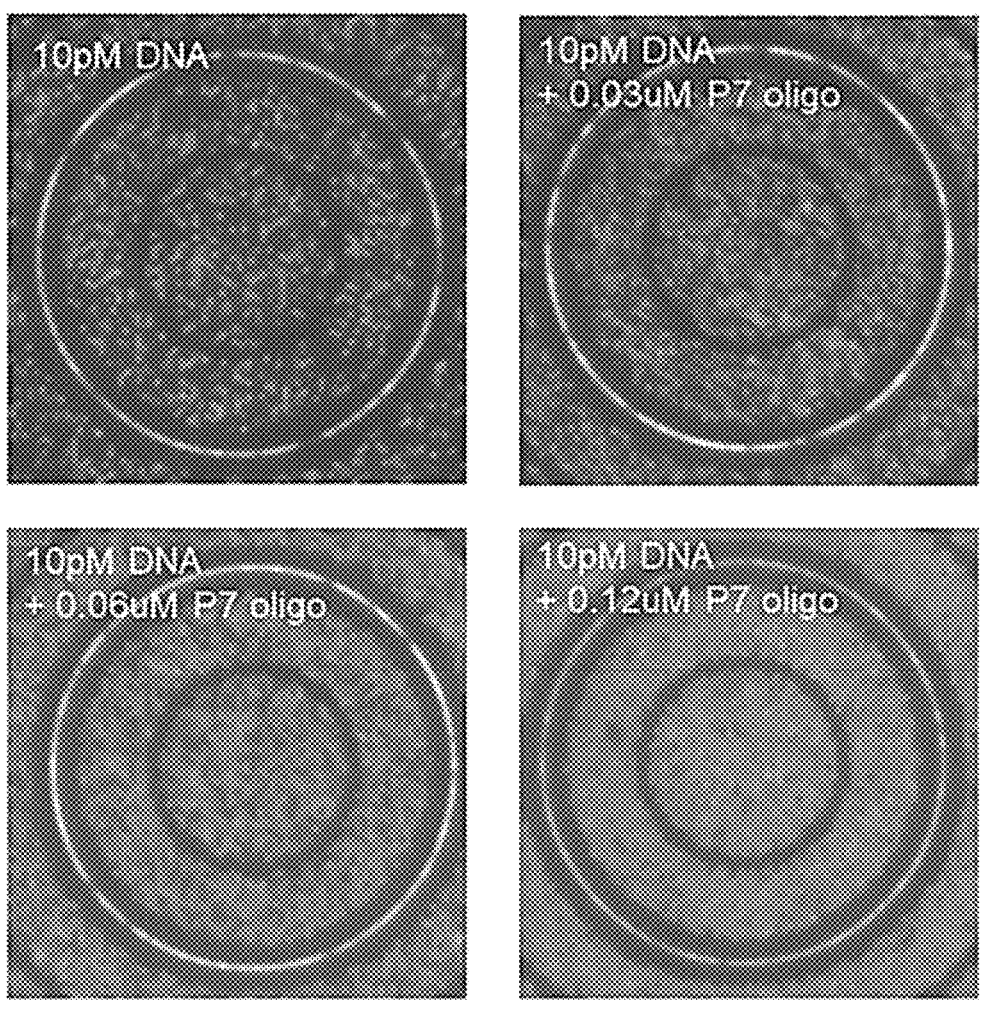

FIG. 9 provides photos of the bottom wells of a patterned flow cell to evaluate whether the amount of amplification can be controlled during the loading process. As shown in the photos, the amount of amplification exhibited a dose dependence relationship to the amount P7 oligo used.

Figure 10:
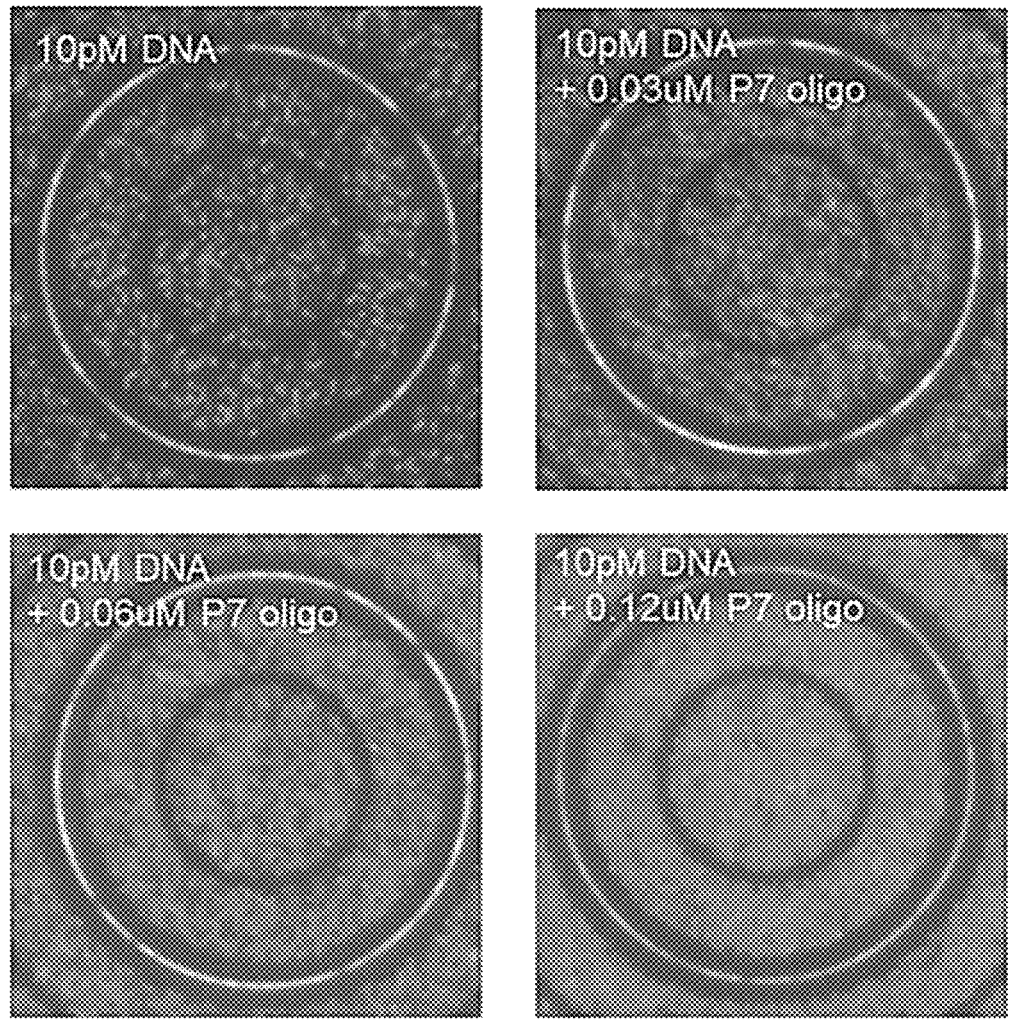

FIG. 10 provides photos of the bottom and tops of wells from a patterned flow cell where the method of disclosure was used to release DNA from the beads using the P7 oligo and seed the wells of a flow cell. As shown in the top two photos, both the top and bottom surfaces of the wells were seeded using the methods of the disclosure. In direct contrast, the top surface of the well was not seeded when just the beads were used (bottom right photo), while the bottom surface of the well was minimally seeded when just the beads were used (bottom left photo).

The accompanying drawings, which are incorporated into and constitute a part of this specification, illustrate one or more embodiments of the disclosure and, together with the detailed description, serve to explain the principles and implementations of the disclosure.

DETAILED DESCRIPTION

As used herein and in the appended claims, the singular forms "a," "an," and "the" include plural referents unless the context clearly dictates otherwise. Thus, for example, reference to "a flow cell" includes a plurality of such flow cells and reference to "the DNA library" includes reference to one or more DNA libraries, and so forth.

Also, the use of "or" means "and/or" unless stated otherwise. Similarly, "comprise," "comprises," "comprising," "include," "includes," "including," "have," "haves," and "having" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The term "amplifying" or "amplification" herein is intended to mean the process of increasing the number of a template polynucleotide sequence by producing copies of the template. The amplification process can be either linear or exponential. In exponential amplification, the number of copies made of the template polynucleotide sequence increases at an exponential rate. For example, in an ideal exponential amplification reaction of 30 rounds, one copy of template DNA will yield $2^{30}$ or 1,073,741,824 copies. However, bridging amplification as described herein does not typically occur under ideal conditions, and a 30-cycle "exponential" reaction may only yield a few hundred to a few thousand copies of the original template, mainly due to the limited localized concentration of surface bound primers and the competition with template re-hybridization. In linear amplification the number of copies made of the template polynucleotide sequences increases at a linear rate. For example, in an ideal 4-hour linear amplification reaction with a copying rate of 2000 copies per minute, each copy of template DNA will yield 480,000 copies. In a certain embodiment, the compositions, methods and kits of the disclosure provide for linear amplification reactions to release polynucleotide from beads.

The term "capture agent" refers to agent present on the surface of a flow cell that is capable of binding to target biomolecule, typically a nucleic acid-based biomolecule, such that the target biomolecule becomes immobilized on the surface of a flow cell. In particular, the "capture agent" is specific to a target biomolecule and does not bind to non-target biomolecules or other compounds. Exemplary capture agents include receptors and/or ligands having a respective binding partner attached to target nucleic acids, examples of which are set forth previously herein. A particularly useful capture agent is a capture nucleic acid that is complementary to a sequence of one or more target nucleic acids. For example, capture nucleic acids that are present on the surface of a flow cell can have a universal capture sequence that is complementary to a universal sequence that is present in the target nucleic acids. In some embodiments, the capture nucleic acid can also function as a primer for amplification of the target nucleic acid (whether or not it also contains a universal sequence). A universal capture sequence can include, e.g., a region having the sequence of a universal Illumina® capture primer or a region specifically hybridizing with a universal Illumina® capture primer. Universal Illumina® capture primers include, e.g., P5 5'-AATGATACGGCGACCACCGA-3' ((SEQ ID NO: 1)) or P7 (5'-CAAGCAGAAGACGGCATACGA-3' (SEQ ID NO: 2)), or fragments thereof. A region specifically hybridizing with a universal Illumina® capture primer can include, e.g., the reverse complement sequence of the Illumina® capture primer P5 ("anti-P5": 5'-TCGGTGGTCGCCGTATCATT-3' (SEQ ID NO: 3) or P7 ("anti-P7": 5'-TCGTATGCCGTCTTCTGCTTG-3' (SEQ ID NO: 4)), or fragments thereof. Other capture nucleic acids can include a universal capture sequence and a target-specific capture region. The capture nucleic acid can further include a sequencing primer binding site (SBS), a target-specific capture region, a predetermined cleavage site, such as a restriction site, and a linker region, e.g., a linker region separating two or more restriction sites. Some capture primers can include, e.g., a universal capture region and an SBS. A SBS can include, e.g., a region having the sequence of an Illumina® sequencing primer, or fragment thereof, or a region specifically hybridizing with an Illumina® sequencing primer, or fragment thereof. Illumina® sequencing primers include, e.g., SBS3 (5'-ACACTCTTTCCCTACACGACGCTCTTCCGATCT-3' (SEQ ID NO: 5)) or SBS8 (5'-CGGTCTCGGCATTCCTGCTGAACCGCTCTTCCGATCT-3' (SEQ ID NO: 6)). A region specifically hybridizing with an Illumina® sequencing primer, or fragment thereof, can include, e.g., the reverse complement sequence of the Illumina® sequencing primer SBS3 ("anti-SBS3": 5'-AGATCGGAAGAGCGTCGTGTAGGGAAAGAGTGT-3'(SEQ ID NO: 7)) or SBS8 ("anti-SBS8": 5'-AGATCGGAAGAGCGGTTCAGCAGGAATG CCGAGACCG-3' (SEQ ID NO: 8)), or fragments thereof. A capture nucleic acid can have any combination of regions, e.g., any combination of Illumina® P5, P7, SBS3, or SBS8 primer regions, or fragments thereof, including combinations such as P5-SBS3 and P7-SBS8, or fragments thereof.

A capture nucleic acid can be blocked at the 3'-end (3'-blocked) or unblocked at the 3'-end (3'-unblocked). Capture nucleic acids with blocked 3'-ends can, e.g., be 3'-phosphate terminated. Some capture nucleic acids with blocked 3'-ends can be deblocked. Deblocking can occur in an enzymatic reaction or a chemical reaction. The enzymatic reaction can be mediated, e.g., by a kinase or a phosphatase. For example, a 3'-phosphate-terminated primer can be deblocked by a kinase, such as T4 kinase.

A capture nucleic acid can include a predetermined (non-random) cleavage site. Possible predetermined cleavage sites are disclosed, e.g., in U.S. Pat. No. 8,715,966 B2. Cleavage at predetermined sites can occur, e.g., as enzymatic cleavage or non-enzymatic cleavage, such as chemical cleavage. Enzymatic cleavage at a predetermined site, such as restriction sites, can be mediated, e.g., by a restriction enzyme, such as a restriction endonuclease. In some embodiments, a predetermined cleavage site in a primer can include a uracil base. Cleavage can occur through the treatment of the uracil containing primer with a uracil DNA glycosylase, to form an a basic site in the primer, followed by treatment with an endonuclease, heat or alkali, to cleave the primer at the a basic site. In some embodiments, the predetermined cleavage site includes a diol linker, which can be cleaved by treatment with periodate. In some embodiments, the predetermined cleavage site includes an 8-oxo-guanine.

The predetermined cleavage site can include an enzyme restriction site. Any restriction enzyme or any enzyme restriction site known to a skilled artisan can be used in a method or composition provided herein. For example, the restriction endonuclease can be a Type I enzyme (EC 3.1.21.3), a Type II enzyme (EC 3.1.21.4), a Type III enzyme (EC 3.1.21.5), or a Type IV enzyme (EC 3.1.21.5). Restriction endonucleases can include, for example, without limitation, Alu I, Ava I, Bam HI, Bgl II, Eco P15 I, Eco RI, Eco RII, Eco RV, Hae III, Hga I, Hha I, Hind III, Hinf I, Hpa I, Kpn I, Mbo I, Not I, Pst I, Pvu II, Sac I, Sal I, SapI, Sau 3A, Sca I, Sma I, Spe I, Sph I, Sst I, Stu I, Taq I, Xba I or Xma I. The restriction endonuclease can be a recombinant restriction enzyme. Recombinant restriction enzymes can include, without limitation, fusion proteins including a natural or engineered DNA binding domain (e.g., zinc finger domains, TAL effector domains) and a nuclease domain (e.g., the cleavage domain of the Type IIS restriction enzyme Fokl).

In particular embodiments, a capture agent, such as a capture nucleic acid, can be attached to specific features arrayed on the surface of a patterned flow cell. For example, the capture agent can be attached to the surface of a feature (e.g., wells) of an array on a patterned flow cell. Alternately, the capture agents are bound to the surface of a flow cell in a random manner (i.e., a non-patterned flow cell). The attachment can be via an intermediate structure such as a bead, particle or gel. Attachment of capture nucleic acids to feature of an array of patterned flow cell by use of gel is described in WO 2008/093098, which is incorporated herein by reference. Exemplary gels that can be used in the methods and apparatus set forth herein include, but are not limited to those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, US Pat. App. Pub. No. 2014/0079923A1, U.S. Pat. No. 9,815,916B2, and U.S. Pat. No. 10,208,142B2, the disclosures of which are incorporated herein by reference). In regards to PAZAM the capture agents may be bound to residual azide on the PAZAM surface by using click chemistry.

As used herein, the term "clonal population" refers to a population of nucleic acids that are homogeneous with respect to a particular nucleotide sequence. The homogenous sequence can be at least 10 nucleotides long, or longer, for example, at least 50, 100, 250, 500 or 1000 nucleotides long. A clonal population can be derived from a single target nucleic acid or template nucleic acid. Essentially all of the nucleic acids in a clonal population have the same nucleotide sequence. It will be understood that a small number of mutations (e.g., due to amplification artifacts) can occur in a clonal population without departing from clonality.

The terms "denature" and "denaturation" are broad terms which refer primarily to the physical separation of the DNA bases that interact within for example, a Watson-Crick DNA-duplex of the single stranded polynucleotide sequence and its complement. The terms also refer to the physical separation of both of these strands. In their broadest sense the terms refer to the process of creating a situation wherein annealing of another primer oligonucleotide or polynucleotide sequence to one or both of the strands of a duplex becomes possible.

As used herein, the term "flow cell" is intended to mean a chamber having a surface across which one or more fluid reagents can be flowed and to which nucleic acids can bind and seed the surface(s) of the flow cell. Generally, a flow cell will have an ingress opening and an egress opening to facilitate flow of fluid. Examples of flow cells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In a certain embodiment, a flow cell includes a solid support having a surface on which nucleic acids can bind. In some embodiments, the surface contains a lawn of capture agents that can bind to released polynucleotides from beads. In some examples, the surface is a patterned surface. A "patterned surface" refers to an arrangement (such as an array) of different regions (such as amplification sites) in or on an exposed surface of a solid support. For example, one or more of the regions can be features where one or more capture agents are present. The features can be separated by interstitial regions where the capture agents are not present. In some embodiments, the pattern can be an x-y format of features that are in rows and columns. In some embodiments, the pattern can be a repeating arrangement of features and/or interstitial regions. In some examples, the pattern can be a random arrangement of features and/or interstitial regions. In some embodiments, the surface is a patterned surface that contains an array of wells with capture agents that bind to released polynucleotides from beads, with interstitial regions between the wells that lack the capture agents. In several cases the substrates are exemplified in these references for applications that use beads in the wells. The patterned flow cells can be used with the compositions, methods and kits of the present disclosure.

A patterned flow cell comprises an array of features, such as microwells or nanowells, on glass, silicon, plastic or other suitable solid supports. The array of features can comprise capture agents which, in one embodiment, are covalently-linked to a gel on the surface of the well, such as poly(N-(5-azidoacetamidylpentyl) acrylamide) (PAZAM, see, for example, U.S. Pub. No. 2013/184796, WO 2016/066586, and WO 2015/002813, each of which is incorporated by reference herein in its entirety). The lifetime of the flow cell can be extended by covalently linking the polymer to the features on the flow cell surface. However, in many examples the gel need not be covalently linked to the features on the flow cell surface. For example, silane free acrylamide (SFA, see, for example, U.S. Pat. No. 8,563,477, which is incorporated by reference herein in its entirety) can be used as the gel material. SFA is not covalently attached to the features on the flow cell surface. Examples of flow cells with patterned surfaces that can be used in the methods set forth herein are described in U.S. Pat. Nos. 8,778,848, 8,778,849 and 9,079,148, and U.S. Pub. No. 2014/0243224, each of which is incorporated by reference herein in its entirety. The array of features on the surface of flow cells can be used to capture a single nucleic acid template molecule to seed subsequent formation of a homogenous colony, for example, via bridge amplification. Such patterned arrays are particularly useful for nucleic acid sequencing applications.

The array of features on the flow cell surface can have at any of a variety of densities including, for example, at least about 10 (such as at least about 100, at least about 500, at least about 1000, at least about 5,000, at least about 10,000, at least about 50,000, at least about 100,000, at least about 1,000,000, or at least about 5,000,000, or more) features/cm$^2$.

An array of features (e.g., wells) on the surface of a patterned flow cell can appear as a grid of spots or patches. The features can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful. The pitch can be the same between different pairs of nearest neighbor features or the pitch can vary between different pairs of nearest neighbor features. In particular embodiments, the features (e.g., wells) of an array of the patterned flow cell can each have an area that is larger than about 100 nm$^2$, 250 nm$^2$, 500 nm$^2$, 1 μm$^2$, 2.5 μm$^2$, 5 μm$^2$, 10 μm$^2$, 100 μm$^2$, or 500 μm$^2$. Alternatively or additionally, features (e.g., wells) of an array can each have an area that is smaller than about 1 mm$^2$, 500 μm$^2$, 100 μm$^2$, 25 μm$^2$, 10 μm$^2$, 5 μm$^2$, 1 μm$^2$, 500 nm$^2$, or 100 nm$^2$. Indeed, a region can have a size that is in a range between an upper and lower limit selected from those exemplified above.

An array of features (e.g., wells) on a patterned flow cell surface can be discrete, being separated by interstitial regions. The size of the features and/or spacing between the regions can vary such that arrays can be high density, medium density or lower density. High density arrays are characterized as having features separated by less than about 15 μm. Medium density arrays have features separated by about 15 to 30 μm, while low density arrays have regions separated by greater than 30 μm. An array can have regions that are separated by less than 100 μm, 50 μm, 10 μm, 5 μm, 1 μm or 0.5 μm. Interstitial regions that have a substantially lower quantity or concentration of capture agents, compared to the features of the array, are advantageous. Interstitial regions that lack capture agents are particularly advantageous. For example, a relatively small amount or absence of capture agents at the interstitial regions favors localization of target nucleic acids, and subsequently generated clusters, to desired features. In particular embodiments, the features can be concave features in a surface (e.g., wells) and the features can contain a gel material. The gel-containing features (e.g., PAZAM) can be separated from each other by interstitial regions on the surface where the gel is substantially absent or, if present the gel is substantially incapable of supporting localization of nucleic acids. Methods and compositions for making and using substrates having gel containing features, such as wells.

As used herein, the term "flow cell surface" means a part of a flow cell that is accessible to contact with reagents, beads or analytes. The flow cell surface can be substantially flat or planar. Alternatively, the flow cell surface can be rounded or contoured. Exemplary contours that can be included on a flow cell surface are wells, depressions, pillars, ridges, channels or the like. The flow cell surface can be comprised of a material including, but not limited to, glass such as modified or functionalized glass; plastic such as acrylic, polystyrene or a copolymer of styrene and another material, polypropylene, polyethylene, polybutylene, polyurethane or Teflon™; polysaccharides or cross-linked polysaccharides such as agarose or Sepharose; nylon; nitrocellulose; resin; silica or silica-based materials including silicon and modified silicon; carbon-fiber; metal; inorganic glass; optical fiber bundle, or a variety of other polymers. A single material or mixture of several different materials can used to form a surface of a flow cell. Examples of flow cells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211, 414; 7,315,019; 7,405,281, and US 2008/0108082, each of which is incorporated herein by reference.

The term "isothermal" as used herein refers to processes in which the temperature of a system or device remains constant, i.e., wherein ΔT=0. This optionally occurs when a system/device is in contact with an outside thermal reservoir (for example, a heater, a heat bath, thermoelectric controller (TEC), or the like), and actions or changes occur within the system/device at a rate that allows the system/device to continually adjust to the temperature of the reservoir through heat exchange.

As used herein, the term "polymerase" is intended to be consistent with its use in the art and includes, for example, an enzyme that produces a complementary replicate of a nucleic acid molecule using the nucleic acid as a template strand. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases can use a short RNA or DNA strand, called a primer, to begin strand growth. Some polymerases can displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the terms "polynucleotide" or "nucleic acid" refers to deoxyribonucleic acid (DNA), however where appropriate, the skilled artisan will recognize that the systems and devices herein can also be utilized with ribonucleic acid (RNA). The terms should be understood to include, as equivalents, analogs of either DNA or RNA made from nucleotide analogs. The terms as used herein also encompass cDNA, that is complementary, or copy, DNA produced from an RNA template, for example by the action of reverse transcriptase.

"Primer oligonucleotides" or "primers" are oligonucleotide sequences that are capable of annealing specifically to the single stranded polynucleotide sequences to be amplified under conditions encountered in the primer annealing step of each cycle of an isothermal amplification reaction. Generally, amplification reactions require at least two amplification primers, often denoted "forward" and "reverse" primers. In certain embodiments the forward and reverse primers can be identical. The primer oligonucleotides can include a "template-specific portion," being a sequence of nucleotides capable of annealing to a primer-binding sequence in the single stranded polynucleotide molecule to be amplified (or the complement thereof when the template is viewed as a single strand) during the annealing step. The primer binding sequences generally will be of known sequences and will therefore particularly be complementary to a sequence within known sequence I and known sequence II of the single stranded polynucleotide molecule. The length of the primer binding sequences need not be the same as those of known sequence I or II, and can be shorter, e.g., 16-50 nucleotides, 16-40 nucleotides, or 20-30 nucleotides in length. The optimum length of the primer oligonucleotides will depend upon a number of factors and it is common that the primers are long (complex) enough so that the likelihood of annealing to sequences other than the primer binding sequence is very low.

The polynucleotide molecules to be amplified are typically in single-stranded form, as ssDNA or RNA, or double-stranded DNA (dsDNA) form (e.g., genomic DNA fragments, PCR and amplification products and the like). Thus, a single stranded polynucleotide may be the sense or antisense strand of a polynucleotide duplex. Methods of preparation of single stranded polynucleotide molecules suitable for use in the systems/devices of the disclosure can utilize standard techniques are known in the art, for example heating or treatment with hydroxide followed by dilution. The precise sequence of the primary polynucleotide molecules is generally not material to the disclosure, and may be known or not known. The single stranded polynucleotide molecules can represent genomic DNA molecules (e.g., human genomic DNA) including both intron and exon sequence (coding sequence), as well as non-coding regulatory sequences such as promoter and enhancer sequences. In a particular embodiment, the polynucleotide molecules to be amplified are a DNA library. In a further embodiment, the DNA library is generated using a library preparation kit. In yet a further embodiment, the library preparation kit is from Illumina, Inc (e.g., AmpliSeq™ kits, COVIDSeq™ kit, Illumina DNA prep kits, Illumina RNA prep kits, Nextera™ Kits, SureCell WTA™ Kits, TruSeq™ kits, and TruSight™ kits).

As used herein, the term "recombinase" is intended to be consistent with its use in the art and includes, for example, RecA protein, the T4 uvsX protein, any homologous protein or protein complex from any phyla, or functional variants thereof. Eukaryotic RecA homologues are generally named Rad51 after the first member of this group to be identified. Other non-homologous recombinases may be utilized in place of RecA, for example, RecT or RecO.

As used herein, the term "single stranded binding protein" is intended to refer to any protein having a function of binding to a single stranded nucleic acid, for example, to prevent premature annealing, to protect the single-stranded nucleic acid from nuclease digestion, to remove secondary structure from the nucleic acid, or to facilitate replication of the nucleic acid. The term is intended to include, but is not necessarily limited to, proteins that are formally identified as Single Stranded Binding proteins by the Nomenclature Committee of the International Union of Biochemistry and Molecular Biology (NC-IUBMB). Exemplary single stranded binding proteins include, but are not limited to E. coli SSB, T4 gp32, T7 gene 2.5 SSB, phage phi 29 SSB, any homologous protein or protein complex from any phyla, or functional variants thereof.

"Solid-phase amplification" as used herein refers to nucleic acid amplification reactions carried out on the surface of a channel of a flow cell so that all or a portion of the amplified products are immobilized on the solid support as they are formed.

Library preparation is an important first step for all next-generation sequencing (NGS) applications and generally employs several common steps. In vitro transposition has been used to generate sequencer-ready libraries from genomic DNA (gDNA) with dramatic time savings and reduced input requirements than previous methods. Transposome-based library construction improves the DNA library preparation process by eliminating the need for a separate DNA fragmentation step and removing the prerequisite for ligation between DNA fragments. The efficiency of fragmentation is highly dependent on the enzyme to DNA ratio. Thus, variable DNA input amounts will generate inconsistencies in the fragment size distribution of the library. This introduces variability in the library preparation process that can have downstream effects on sequencing coverage.

Bead-linked transposome technology has been used for preparing libraries for whole genome sequencing technologies (e.g., Illumina™ DNA prep) as well as targeted sequencing applications (e.g., Illumina™ DNA prep for Enrichment). This methodology utilizes a known concentration of transposomes conjugated directly to beads to bind a fixed amount of DNA. This therefore offers broad applicability, supporting a wide spectrum of DNA input ranges as well as integrated extraction of blood and saliva samples generating normalized libraries for sequencing to facilitate a quantification-free workflow. Libraries generated outside the standard parameters of the workflow, highlighting novel applications for whole genome sequencing, including human genome builds and variant calling from below 1 ng DNA input, customization of insert size, and preparation of libraries from short fragments and severely degraded samples. For large and complex genomes, coverage across the genome, including difficult regions, was improved compared with other library preparation methods. Libraries were successfully generated from amplicons of varying sizes (from 50 bp to 11 kb), however, a decrease in efficiency was observed for amplicons smaller than 250 bp. On-bead tagmentation chemistry is also applicable for targeted sequencing and supports a wide range of DNA input amounts, various sample types, and a broad range of applications, including fixed panels, custom panels, and whole-exome sequencing. The bead-linked transposomes can therefore be effectively used for whole genome sequencing as well as for targeted resequencing. The source of DNA can be from the environment, from a subject's sample, etc. DNA can be extracted from virtually any part of a subject's body. For example, the input DNA can be extracted from a variety of sample types, including but not limited to, urine, blood, saliva, tissue, serum, plasma, sputum, bile, fecal, hair, skin, and/or primary cell sample.

Implementations provided herein include capture of polynucleotides released from bead-linked transposomes disclosed herein on a surface of a flow cell. The bead-linked transposomes are loaded into the flow cell and using the methods of the disclosure, polynucleotides are released from the bead-linked transposomes and are seeded on the surface(s) of the flow cell.

In some examples, the bead-linked transposomes or polynucleotides released from the bead-linked transposomes are captured on the surface of a flow cell by the interaction of a capture agent on a surface of the flow cell with the released polynucleotide or with the transposome bead. Examples of capture agents for immobilizing a transposome bead on the surface of a flow cell in the disclosed methods include, without limitation, a capture nucleic acid that is complementary to at least a portion of a nucleic acid linked to an adaptor on the bead, or to a portion of a nucleic acid released from the transposome bead; or to a member of a receptor-ligand binding pair (e.g., avidin, streptavidin, biotin, lectin, carbohydrate, nucleic acid binding protein, epitope, antibody, etc.) capable of binding to a target nucleic acid (or linking moiety attached thereto); or to a chemical reagent capable of forming a covalent bond with a target nucleic acid (or linking moiety attached thereto).

In some examples, the capture agent is a first member of a specific binding pair that is located on the flow cell, and binds to a second member of the specific binding pair located on the transposome bead or to a polynucleotide released from the bead. For example, the flow cell is functionalized with a first member of a specific binding pair and the polynucleotide released from the bead comprises the second member of the specific binding pair.

In some examples, the capture agent is present at segregated locations on the flow cell. For example, in examples where the flow cell is a patterned flow cell containing an array of wells, the capture agent can be present at wells of the patterned flow cell.

Additionally, flow cells may contain bead trapping structures such as pillars/posts, weirs, cup-shaped structures, to immobilize/capture the beads in defined location within the flow cell. These trapping structures can be made by etching in glass or silicone, or by photolithography of photo patternable materials.

In a particular embodiment, the disclosure describes methods that enhance or improve seeding efficiency of flow cells with bead-linked transposomes comprising the step of: transposing nucleic acids onto a transposome bead. After transposition, both 5' ends of the transposed strands are linked to the bead-linked transposomes via a strong biotin/streptavidin linkage. This has so far required the use of excess biotin and heat to release the molecules from the beads. Heat also leads to increased diffusion in the flow cell, which will disrupt the spatial co-location of the clusters formed. The disclosure provides an improved or enhanced method to improve nucleic acid release and flow cell seeding that does not require the use of heat or excess biotin.

In another embodiment, the disclosure describes methods that enhance or improve seeding efficiency of flow cells with bead-linked transposomes comprising the step of: releasing nucleic acids from a transposome bead and seeding the nucleic acids onto one or more surfaces of a flow cell, so that closely linked nucleic acids are spatially co-located on the select locations of the surface of the flow cell. The spatial co-localization of the nucleic acids on the flow cell surface acts as a form of indexing, thereby enabling sequencing reads to be linked together into contigs.

In a certain embodiment, the methods of the disclosure are advantageously, PCR-free. In another embodiment, the methods of the disclosure exhibit high efficiency of release/seeding such that almost all the transposed molecules are captured on one or more surfaces of a flow cell. Typically, nucleic acid molecules are released from beads by the use of heat/excess biotin. However, one shortcoming of use of said techniques is that patterned flow cells require 2-3 molecules or more to efficiently seed nanowells, and the use of standard methodologies are not overly efficient, resulting in reduced efficiency of capture of the transposed molecules and hence lead to more "holes" in coverage for each contig. In comparison to standard techniques, the method of the disclosure provides for improved or enhanced release and seeding efficiency of flow cells with polynucleotides.

Figure 1:
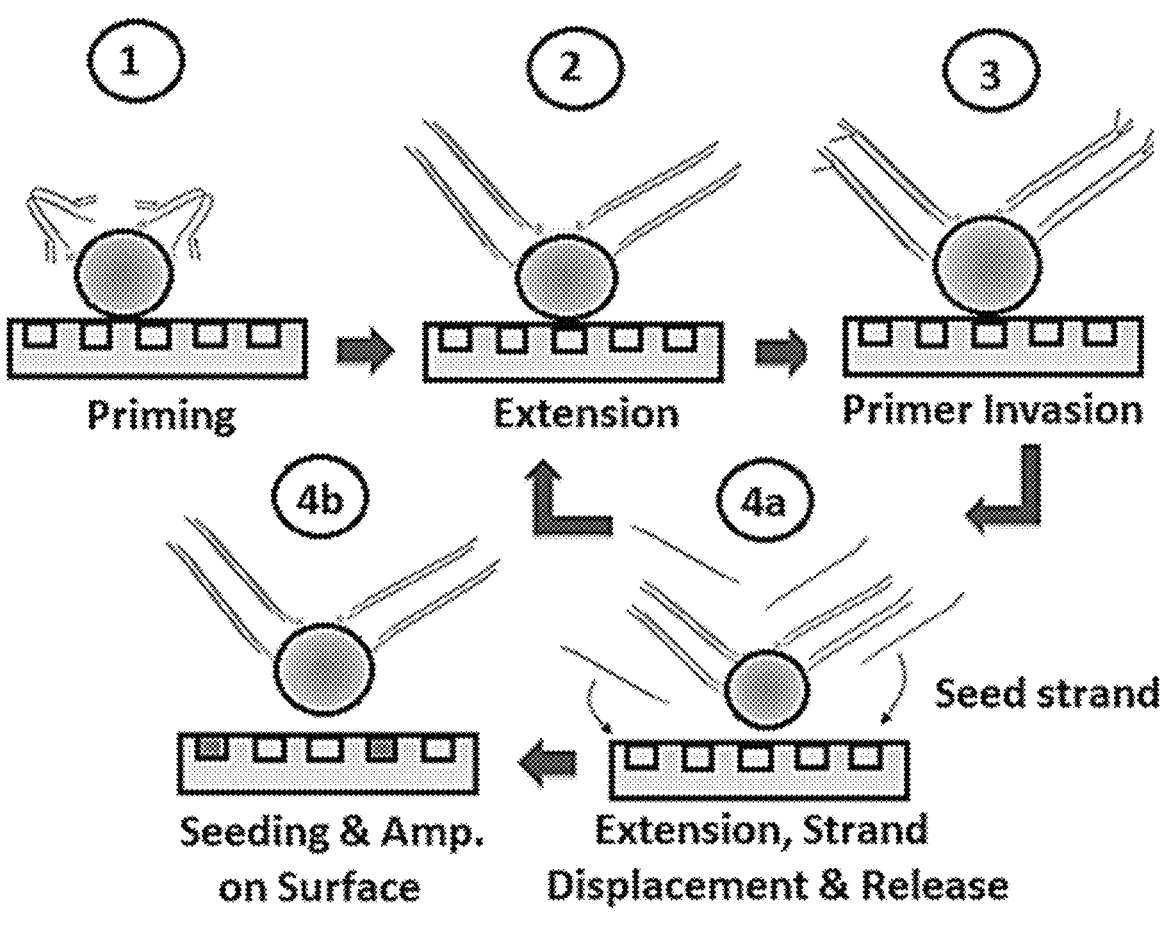
FIG. 1 provides an overview of the steps making up an exemplary method of the disclosure to enhance or improve seeding efficiency of flow cells with transposome beads. As shown, step 1 provides for priming off the 3' ends of Y-type adaptors on the beads with a primer, like P7 or P5, in solution. Step 2 provides for extension from the bound primers to make a double stranded nucleic acid product by using exclusion amplification. Then, in step 3, as the extension products are formed using exclusion amplification, the products displace the previously copied strand into solution, step 4a. The released strands then seed the surface of the flow cell, step 4b, for analysis and applications.

FIG. 1 provides an exemplary embodiment of a method of the disclosure that is used to enhance or improve seeding efficiency of flow cells with bead-linked transposomes. As shown, the method uses a solution primer (e.g., P7) to prime off the 3' ends of the Y-type adaptors on the beads (step 1). Exclusion amplification is used to extend the primers to make the dsDNA structures seen in step 2. Then, further strand invasion occurs via more P7 primer and a recombinase (step 3). As these are extended by the polymerase, the product will displace the previously copied strand into solution (step 4a), which is then available for seeding and amplification onto the surface (step 4b). As the P7/exclusion amplification mix is incubated with the beads, additional rounds of extension, primer invasion and release are carried out, leading to linear copying of the strands from the bead. The results of which, overcome the need for multiple strands to seed each nanowell of a patterned flow cell, that further is not prone to the bias of a typical 2 primer solution PCR (so maintaining the good GC bias of a PCR-free library).

Figure 2:
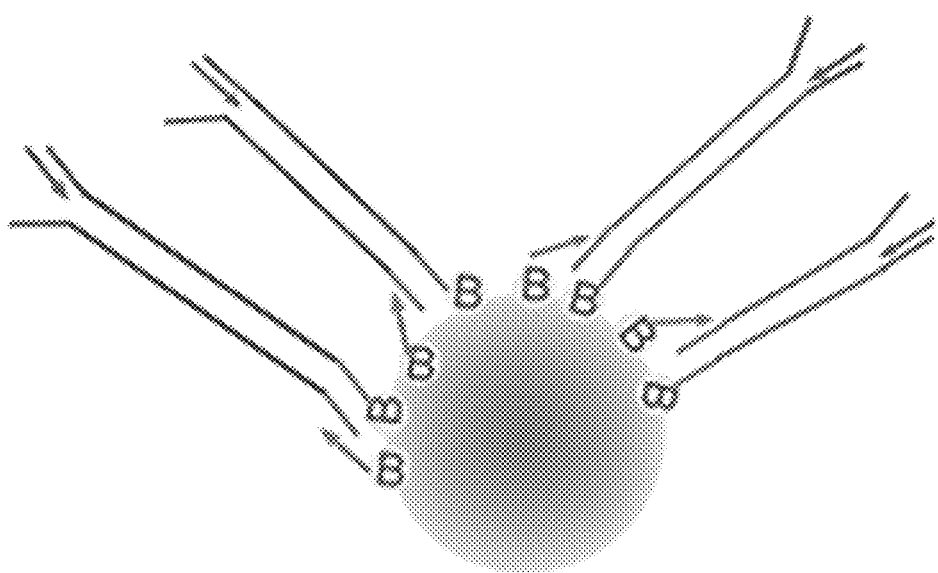
FIG. 2 provides an embodiment of a method of the disclosure where the beads comprise an amplification primer (e.g., P5) that has a different sequence than the primer (e.g., P7) in solution.

An additional embodiment of the disclosure is shown in FIG. 2, where an amplification primer that is different from the solution primer is included on the bead. For example, the bead can comprise an amplification primer, like P5. Accordingly, at step 3 of FIG. 1, in addition to the solution primer (e.g., P7) binding to the adaptor, there would be additional primer invasion at the bead surface by the amplification primer (e.g., P5). Resulting, in even more copies being made from each strand, more like an exponential type amplification rather than a linear one. While use of an amplification primer may introduce PCR-type bias, the method is surface based amplification rather than bulk solution-based PCR, i.e., less competition for reagents. For instance, cluster-based surface amplification is less biased than nano library amplification. This concept is illustrated in FIG. 2.

Figure 3:
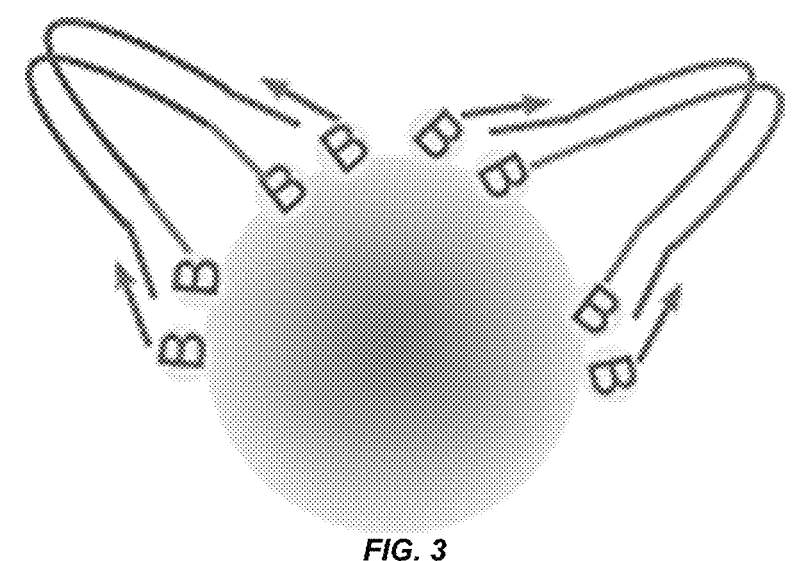
FIG. 3 provides an embodiment of a method of the disclosure where the beads comprise an amplification primer (e.g., P7) that has the same or nearly the same sequence as the primer (e.g., P7) in solution.

An alternative embodiment of a method of the disclosure is shown in FIG. 3. In this embodiment, the bead comprises an amplification primer that is the same as the solution primer (e.g., both P7). Exclusion amplification (e.g., ExAMP) is then used for localized linear amplification onto the amplification primer surrounding each transposition event. After which, the beads are introduced into the flow cell and either (a) using a heat/excess biotin means to release the amplified polynucleotides from streptavidin/biotin links, or (b) using exclusion amplification (e.g., ExAmp) and a second solution primer means to release amplified poly-nucleotides via invasion/displacement. The latter means would further provide for amplification across the surface of the bead.

A further alternate embodiment of a method of the disclosure is for the bead to comprise two or more different types of amplification primers (e.g., P5 and P7). In this embodiment, after transposition, surface-based clustering of the library can be carried out with amplification. After which, the beads are introduced into the flow cell and either (a) using a heat/excess biotin means to release the amplified polynucleotides from streptavidin/biotin links, or (b) using exclusion amplification (i.e., ExAmp) and a solution primer means to release amplified polynucleotides via invasion/displacement. In regards to the latter means, a solution primer correlating to one or the other amplification primer can be used, or solution primers correlating to multiple types of amplification primers are used. The amplification primers on the beads should be inert to transposition, or made to be inert by use of single stranded binding proteins and the like.

Figure 4:
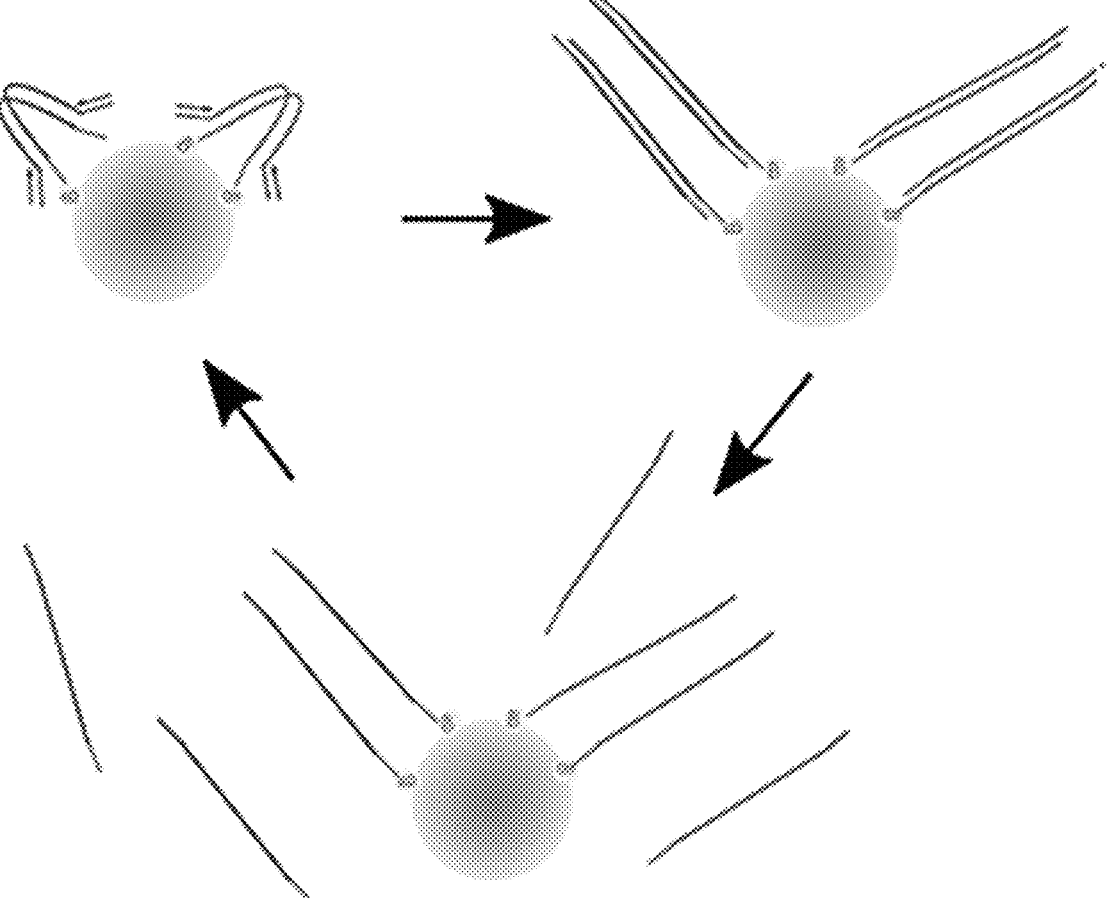
FIG. 4 provides an embodiment of a method of the disclosure where a Bridge Amplification approach is used to amplify the library on the beads and seed the amplified product onto the surface(s) of a flow cell.

FIG. 4, provides an embodiment of a method of the disclosure where a Bridge Amplification approach is used to amplify the library on the beads and seed the amplified product into nanowells. In this approach, a soluble primer is first hybridized to the library and extended using an amplification mix (e.g., AMS). The library is then denatured off the beads by raising temperature to >80° C. after flowing in a 40% a formamide/HT1 mixture. The denatured library strand is seeded by lowering the temperature to 20° C. Then, another round of extension and denaturation is performed by exchanging the reagents.

Figure 5:
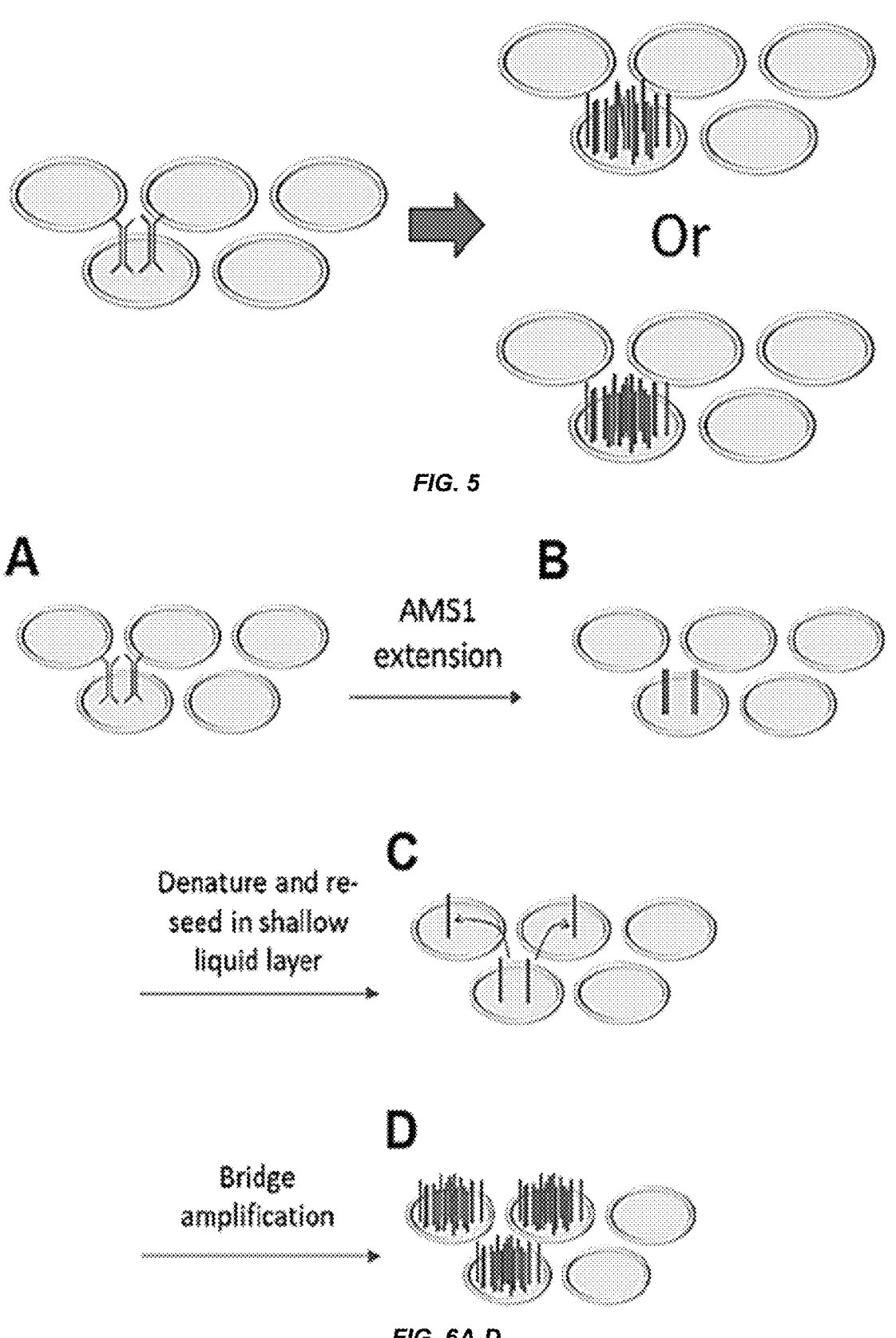
FIG. 5 demonstrates that when two or more DNA library molecules are seeded in the same well of the patterned flow cell, either one dominant cluster (blue) results or two (or more) equivalent polyclonal clusters (blue+pink) result.

The compositions, methods and kits disclosed herein are directed to efficiently releasing polynucleotides from beads that are the seeded and amplified on the surface of flow cells in order to provide readable clusters for maximal molecular coverage of the polynucleotides. As illustrated in FIG. 5, once two or more DNA library molecules are seeded onto the same well of a patterned flow cell, it either ends with only one dominant cluster or two or more equivalent clusters that result in poly-clonality. In both cases, there is a loss of the valuable information from the polynucleotides that failed to become heathy clusters.

In order to provide even more extensive seeding of a patterned flow cell, the disclosure provides on-flow cell linear amplification/shallow layer denaturing process that provides more efficient and extensive seeding within the cluster cloud area. As illustrated in FIG. 6A-D, after seeding the polynucleotides on the surface of a flow cell, the polynucleotides are copied using low temperature first extension with Illumina™ AMS1. Then a "shallow layer liquid" denaturing and seeding step is used to re-seed nearby well with the copied polynucleotides. The reagent used for single pot denaturing/seeding is the mixture of LDR (formamide) and HT1. A bridge amplification step is then used. Using the foregoing process, the sequencing info from all the polynucleotides released from the beads can be realized.

In a particular embodiment, the problem of low seeding efficiency from bead-linked transposomes on patterned flow cells is solved by using exclusion amplification (e.g., ExAmp) with a solution primer to copy transposed templates on the beads. Subsequent strand invasion by more solution primers will then lead to displacement of the copied strands into solution, thereby effectively releasing them from the beads and allowing them to seed the surface(s) of the flow cell in proximity to the bead. Further embodiments of this method can include bead bound amplification primers, to enhance amplification and displacement of the bead bound templates.

The methods set forth herein can be used to generate various densities of clusters on a flow cell surface. For example, a flow cell surface can comprise a cluster density $(K/mm^2)$ of about 5, 10, 50, 100, 150, 200, 250, 300, 350, 400, 450, 500, 550, 600, 650, 700, 750, 800, 850, 900, 950, 1000, 1100, 1050, 1200, 1250, 1300, 1350, 1400, 1450, 1500, 1550, 1600, 1650, 1700, 1750, 1800, 1850, 1900, 1950, 2000, 2500, 3000, 4000, 5000, or a range of densities including or between any two of the foregoing values. The density of the clusters is related to the number of beads used and the size of the beads.

Nucleic acids can be bound to a bead by single point covalent attachment to the surface at or near the 5' end of the nucleic acid, or at or near the 3' end of the nucleic acid. In embodiments where the nucleic acid serves as an amplification primer, attachment is configured to leave the template-specific portion of the primer free to anneal to its cognate template and the 3' hydroxyl group free for primer extension. Any suitable covalent attachment agents known in the art may be used for this purpose. The chosen attachment chemistry will depend on the nature of the bead surface, and any derivatization or functionalization applied to it. Examples of attachment agents can include, but are not limited to, biotin/streptavidin linkage, a covalent bond, base pairing between two complementary sequences, an antibody binding an antigen, an antibody binding another antibody, a polyhistidine tag binding a carrier comprising a metal ion, and a receptor binding a ligand. The amplification primer bound to the bead may include a moiety, which may be a non-nucleotide chemical modification, to facilitate attachment. In a certain embodiment, the amplification primer may include a biotin residue at the 5' end that can form a linkage with streptavidin or avidin on the bead's surface. In another embodiment, the amplification primer may include a sulfur-containing nucleophile, such as phosphorothioate or thiophosphate, for example, located at the 5' end. In the case of polyacrylamide-based beads, this nucleophile will bind to a bromoacetamide group present on the bead's surface. Attachment can also occur via ligand receptor interactions such as those set forth elsewhere herein.

The beads used with the patterned flow cells disclosed herein are comprised of a polymeric material (e.g., polystyrene or polystyrene divinylbenzene), a silica material, a zirconia material, and/or a superparamagnetic material, etc., which has been "functionalized", for example by application of a layer or coating of a material comprising reactive groups which permit covalent attachment of nucleic acids or other biomolecules. Examples of such coatings include, but are not limited to, streptavidin, amine groups, carboxyl groups, epoxy groups, tosyl groups, or ligands (e.g., receptors, receptor ligands, etc.). In such embodiments, the polynucleotides may be directly covalently attached to reactive groups (e.g., tosyl groups) in the layer or coating on the beads, but the coating or layer may itself be non-covalently attached to the bead. In a further embodiment, the beads disclosed herein can have several layers and that the layers can have different compositions. The beads disclosed herein are generally spherical, but may also be ovoid. The beads may comprise a generally hydrophilic surface or a generally hydrophobic surface. The beads have a diameter of about 500 nm, 1 μM, 1.1 μM, 1.2 μM, 1.3 μM, 1.4 μM, 1.5 μM, 1.6 μM, 1.7 μM, 1.8 μM, 1.9 μM, 2 μM, 2.1 μM, 2.2 μM, 2.3 μM, 2.4 μM, 2.5 μM, 2.6 μM, 2.7 μM, 2.8 μM, 2.9 μM, 3 μM, 3.1 μM, 3.2 μM, 3.3 μM, 3.4 μM, 3.5 μM, 3.6 μM, 3.7 μM, 3.8

µM, 3.9 µM, 4 µM, 4.1 µM, 4.2 µM, 4.3 µM, 4.4 µM, 4.5 µM, 4.6 µM, 4.7 µM, 4.8 µM, 4.9 µM, 5.0 µM, 5.1 µM, 5.2 µM, 5.3 µM, 5.4 µM, 5.5 µM, 5.6 µM, 5.7 µM, 5.8 µM, 5.9 µM, 6 µM, 6.1 µM, 6.2 µM, 6.3 µM, 6.4 µM, 6.5 µM, 6.6 µM, 6.7 µM, 6.8 µM, 6.9 µM, 7 µM, 7.1 µM, 7.2 µM, 7.3 µM, 7.4 µM, 7.5 µM, 7.6 µM, 7.7 µM, 7.8 µM, 7.9 µM, 8 µM, 8.1 µM, 8.2 µM, 8.3 µM, 8.4 µM, 8.5 µM, 8.6 µM, 8.7 µM, 8.8 µM, 8.9 µM, 9.0 µM, 9.1 µM, 9.2 µM, 9.3 µM, 9.4 µM, 9.5 µM, 9.6 µM, 9.7 µM, 9.8 µM, 9.9 µM, 10 µM, or a range that includes or is in between any two of foregoing distances, including fractional increments thereof. The beads typically comprise a plurality of bound polynucleotides, which may or may not have the same sequence. The number of bound polynucleotides is largely dependent on the size of the bead, and the number of available reactive groups on the beads surface. The beads can be comprised of a variety of materials including controlled pore glass beads, paramagnetic beads, polystyrene, thoria sol, sepharose beads, nanocrystals and others known in the art as described, for example, in *Microsphere Detection Guide* from Bangs Laboratories, Fishers Ind. Beads can be made of biological or non-biological materials. Magnetic beads are particularly useful due to the ease of manipulation of magnetic beads using magnets at various steps of the methods described herein.

The beads disclosed herein typically comprise bead-linked transposomes. Bead-linked transposomes are capable of carrying out on-bead tagmentation on provided DNA templates (e.g., genomic DNA, long template DNA, etc.) The transposomes may be directly attached to the bead using an attachment agent, such as a biotin/streptavidin linkage, a covalent bond, base pairing between two complementary sequences, an antibody binding an antigen, an antibody binding another antibody, a polyhistidine tag binding a carrier comprising a metal ion, and a receptor binding a ligand. Alternatively, the transposomes may be indirectly attached to the bead by using a linker. Examples of linkers can include nucleotides, polymers, peptides, etc. In a particular embodiment, the transposomes are indirectly linked to the bead via an oligonucleotide linker. In such a case, the oligonucleotide linker may comprise terminal sequences that are recognized and bound by transposomes (e.g., mosaic end sequences). The transposase linked to the bead can be transposase Tn5, Sleeping Beauty transposase, Tn7 transposon, or mutations in each of the foregoing to improve activity and/or stability. In particular embodiment, the transposome linked to the bead comprises a transposase Tn5, or mutant or variant thereof. The oligonucleotide linker that links a transposome to the bead, may be attached to the bead using an attachment agent, such as, a biotin/streptavidin linkage, a covalent bond, base pairing between two complementary sequences, an antibody binding an antigen, an antibody binding another antibody, a polyhistidine tag binding a carrier comprising a metal ion, and a receptor binding a ligand. In particular embodiment, the oligonucleotide linker is bound to the bead via a biotin/streptavidin or avidin linkage. The oligonucleotide linker may further comprise one or more barcode sequences, primer sequences, sequencing primer binding sites and/or restriction enzyme recognition sites.

Clusters generated on the surfaces of a flow cell by releasing polynucleotides from immobilized beads can be of similar or smaller size than the area of the surface occupied by the bead from which the cluster was generated, and the clusters will typically be of similar size and intensity to each other. The uniform size, uniform intensity and lack of overlap can provide favorable cluster density per unit area that is higher than that obtainable from other random deposition methods since these other methods often give rise to a surface where clusters may be overlapping and of different sizes and intensities. Images of tightly packed non overlapping clusters having uniform size and intensity are typically easier to analyze than images where a subset of the clusters overlap with each other.

In a particular embodiment, the polynucleotides bound to the beads comprise genomic DNA. In a further embodiment, the polynucleotide strands bound to the bead comprise long template DNA. In yet a further embodiment, the polynucleotide strands bound to the bead comprise DNA from a subject's sample. Examples of samples obtained from a subject include, but are not limited to, urine, blood, saliva, tissue, serum, plasma, sputum, bile, fecal, hair, skin, and/or primary cell sample. The polynucleotide can be bound to a bead using an attachment agent. Examples of attachment agents, include but are not limited to, a biotin/streptavidin linkage, a covalent bond, base pairing between two complementary sequences, an antibody binding an antigen, an antibody binding another antibody, a polyhistidine tag binding a carrier comprising a metal ion, and a receptor binding a ligand.

As the strands are released from the bead by using the methods disclosed herein, the strands bind to capture agents on the surface of the flow cell that is closest to the bead, the proximity of beads to each other in the layer determines the proximity of the polynucleotides that are captured on the flow cell surface. Use of beads to seed a non-patterned flow cell provides for an indirect 'patterned array' based upon the size of the beads used and their packing density on the surfaces of the flow cell. Alternatively, a patterned flow cell can be used with the method disclosed herein. After the strands of the polynucleotide are captured on the flow cell surface (flow cell seeding), a cycle of extension with a polymerase and dNTPs to copy the strand, followed by denaturation, provides a desired array of attached nucleic acids in a single stranded form that can then be subjected to cycles of isothermal amplification. Alternatively, prior to isothermal amplification ((e.g., bridge amplification), seeding efficiency of the flow cell can be further improved by conducting on-flow cell linear amplification of the seeded polynucleotides followed by low volume denaturing and seeding methods disclosed herein. In such an embodiment, various surfaces or features of the flow cell comprises a lawn of single stranded primer sequences, allowing "bridge amplification" to occur. In bridge amplification, when the surface is exposed to conditions suitable for hybridization, the single stranded nucleic acid molecules to be amplified form a bridge so that the adapter sequence on their free end hybridizes with its complementary single stranded primer sequence bound to the surface of the flow cell. Nucleotides and DNA polymerase are then transported into the flow cell to create the complementary strand of the nucleic acid to be amplified. The double stranded sequences created are then denatured by flowing in a denaturing reagent, and the process starts again, thus creating clusters of amplified nucleic acid without changing the temperature of the system during the amplification cycles. In typical embodiments, the majority of the clusters are monoclonal, resulting from the amplification of a single original nucleic acid sequence.

Generally, primer oligonucleotides used to create DNA clusters are single stranded polynucleotides. They may also contain a mixture of natural and non-natural bases as well as natural and non-natural backbone linkages, provided that any non-natural modifications do not preclude function as a primer (i.e., the ability to anneal to a template polynucleotide strand during conditions of the amplification reaction and to act as an initiation point for synthesis of a new polynucleotide strand complementary to the template strand). One of the primers may contain a modification allowing the primer to be removed (cleaved) from the surface to allow the formation of single stranded clusters. Such linearized clusters can undergo hybridization with a further primer strand to allow a sequencing reaction to occur. Extension products can then be generated by carrying out cycles of isothermal amplification on the covalently bound single stranded polynucleotide molecules so that each colony comprises multiple copies of the original immobilized single stranded polynucleotide molecule (and its complementary sequence). One cycle of amplification consists of the steps of hybridization, extension and denaturation. Such steps are generally comparable in terms of reagent components (e.g., buffers, etc.) with traditional nucleic acid amplification procedures such as PCR. Suitable reagents for amplifying nucleic acids (e.g., hybridization, extension, etc.) are well known in the art. Exemplary reagents are described in more detail below.

Thus, a neutralizing/hybridizing buffer can be applied to the single stranded polynucleotide molecules and the plurality of primer oligonucleotides such that the unbound end of a surface bound single stranded polynucleotide molecule hybridizes to a surface bound primer oligonucleotide to form a complex (wherein the primer oligonucleotide hybridizes to and is complementary to a region or template specific portion of the single stranded polynucleotide molecule). This process creates a "bridge" structure. Again, see WO/0246456, U.S. Ser. No. 60/783,618, WO/9844151, and WO/0018957 for further discussion on bridge amplification.

Suitable neutralizing/hybridizing buffers are well known in the art (See Sambrook et al., Molecular Cloning, A Laboratory Manual, 3rd Ed, Cold Spring Harbor Laboratory Press, NY; Current Protocols, eds. Ausubel et al.) as well as the illustration section describing amplification below. Suitable buffers may comprise additives such as betaine or organic solvents to normalize the melting temperate of the different template sequences, and detergents. An exemplary hybridization buffer comprises 2 M betaine, 20 mM Tris, 10 mM Ammonium Sulfate, 2 mM Magnesium sulfate, 0.1% Triton, 1.3% DMSO, pH 8.8.

Next, an extension reaction is done by applying an extension solution comprising an enzyme with polymerase activity and dNTPs to the bridge complexes. The primer oligonucleotide of the complex is extended by sequential addition of nucleotides to generate an extension product complimentary to the single stranded polynucleotide molecule. Suitable extension buffers/solutions are well known in the art (See, e.g., Sambrook et al., Molecular Cloning, A Laboratory Manual, $3^{rd}$ Ed, Cold Spring Harbor Laboratory Press, NY; Current Protocols, eds. Ausubel et al.) and examples below.

Examples of enzymes with polymerase activity that can be used in the systems/devices of the disclosure include DNA polymerase (Klenow fragment, T4 DNA polymerase) and heat-stable DNA polymerases from a variety of thermostable bacteria (such as Taq, VENT, Pfu, Bst and Tfl DNA polymerases) as well as their genetically modified derivatives (TaqGold, VENT exo, Pfu exo, etc.). It will be appreciated that since the amplification reactions performed on the flow cells are isothermal, that additional and/or alternative DNA polymerases can be used as compared to the polymerases for thermal cycling amplification, and, in most embodiments, there is no particular requirement for the polymerase to be thermostable. Also, while enzymes with strand displacing activity such as Bst polymerase show excellent performance in growing effective clusters for sequencing, any DNA polymerase can be used.

The nucleoside triphosphate molecules used to create DNA clusters are typically deoxyribonucleotide triphosphates, for example dATP, dTTP, dCTP, dGTP. The nucleoside triphosphate molecules may be naturally or non-naturally occurring.

After the hybridization and extension steps, the support and attached nucleic acids are subjected to denaturation conditions. Suitable denaturing buffers are well known in the art (See, e.g., Sambrook et al., Molecular Cloning, A Laboratory Manual, $3^{rd}$ Ed, Cold Spring Harbor Laboratory Press, NY; Current Protocols, eds. Ausubel et al.). The systems/devices of the disclosure produce isothermal nucleic acid amplification; therefore, the nucleic acid strands herein are not denatured through temperature elevation or manipulation, but rather by other methods (e.g., chemical, physical, etc.). By way of example, it is known that alterations in pH and low ionic strength solutions can denature nucleic acids at substantially isothermal temperatures. Formamide and urea form new hydrogen bonds with the bases of nucleic acids disrupting hydrogen bonds that lead to Watson-Crick base pairing. These result in single stranded nucleic acid molecules. Alternatively, the strands can be separated by treatment with a solution of low salt and high pH (>12) or by using a chaotropic salt (e.g., guanidinium hydrochloride). In a particular embodiment, sodium hydroxide (NaOH) solution is used at a concentration of from about 0.25M to about 0.1 M. In an alternate embodiment 95% formamide in water, or 100% formamide is used. Such formamide embodiments show additional advantages as the hydroxide treatment can damage the surface and give clusters of lower intensity in some instances. As with the other reagents used, such denaturing reagents are passed through the flow channels.

Following denaturation, two immobilized nucleic acids will be present, the first being the initial immobilized single stranded polynucleotide molecule and the second being its complement, extending from one of the immobilized primer oligonucleotides. Both the original immobilized single stranded polynucleotide molecule and the immobilized extended primer oligonucleotide (the complement) formed are then able to initiate further rounds of amplification by subjecting the support to further cycles of hybridization, extension and denaturation. Such further rounds of amplification will result in a nucleic acid colony or "cluster" comprising multiple immobilized copies of the single stranded polynucleotide sequence and its complementary sequence. The initial immobilization of the single stranded polynucleotide molecule means that the single stranded polynucleotide molecule can only hybridize with primer oligonucleotides located at a distance within the total length of the single stranded polynucleotide molecule. Thus, the boundary of the nucleic acid colony or cluster formed is limited to a relatively local area in which the initial single stranded polynucleotide molecule was immobilized. The terms "cluster" and "colony" are used interchangeably herein to refer to a discrete site on a solid support comprised of a plurality of identical immobilized nucleic acid strands and a plurality of identical immobilized complementary nucleic acid strands. The term "clustered array" or "cluster array" refers to an array formed from such clusters or colonies. In this context the term "array" is not to be understood as requiring an ordered arrangement of clusters.

In typical embodiments, the nucleic acid to be amplified is bound to a bead and immobilized upon the surfaces of a flow cell. The bead-linked transposomes may also be immobilized on the surface of the flow cell. The term "immobilized" as used herein is intended to encompass direct or indirect, covalent or non-covalent attachment, unless indicated otherwise, either explicitly or by context. In certain embodiments of the disclosure, covalent attachment is typically, but generally all that is required is that the molecules (e.g., nucleic acids) remain immobilized or attached to the support under conditions in which it is intended to use the support, for example in applications for amplification. The immobilized nucleic acid molecule for amplification can be obtained either by direct attachment of a suitably modified nucleic acid molecule (either single or double stranded) to a suitably reactive surface, or by hybridization to a surface immobilized primer, followed by a cycle of extension with a polymerase and dNTPs to copy the hybridized strand. The extended strand, or the chemically attached duplex, can then be subject to denaturing conditions to remove the beads and produce the desired immobilized, single stranded nucleic acid molecule that can then be subjected to cycles of isothermal amplification by the instrumentation described herein. The initial step of hybridizing the DNA from solution onto the flow cell can be performed at a higher temperature than the subsequent amplification reactions, which then take place at a substantially isothermal temperature. The hybridization step may also be carried out at the amplification temperature, provided the input nucleic acids strands are supplied to the flow cell surface in a single stranded form attached to the beads.

Some embodiments of preparing a template nucleic acid can include fragmenting a target nucleic acid. In some embodiments, barcoded or indexed adapters are attached to the fragmented target nucleic acid (e.g., DNA library). Adapters can be attached using any number of methods known in the art such as ligation (enzymatic or chemical), tagmentation, polymerase extension, and so forth. In some embodiments, insertion of transposomes comprising non-contiguous transposon sequences can result in fragmentation of a target nucleic acid. In some embodiments comprising looped transposomes, a target nucleic acid comprising transposon sequences can be fragmented at the fragmentation sites of the transposon sequences. Further examples of method useful to fragment target nucleic acids useful with the embodiments provided herein can be found in for example, U.S. Patent Application Pub. No. 2012/0208705, U.S. Patent Application Pub. No. 2012/0208724 and Int. Patent Application Pub. No. WO 2012/061832, each of which is incorporated by reference in its entirety. In a further embodiment, the tagmentated DNA sequences are amplified using a limited-cycle PCR reaction comprising primers that have sequences complementary to the adaptor sequences, the sequences of SEQ ID NO:1 and SEQ ID NO:2, and optionally a barcode or index sequence. In a further embodiment, the sequences amplified using a limited-cycle PCR reaction are of/from a DNA library. In yet a further embodiment, the sequences amplified using a limited-cycle PCR reaction are denatured to single stranded DNA and are selectively bound by biotinylated capture probes that recognize specific sequences and magnetic beads containing streptavidin that interact with the biotinylated capture probes. In a further embodiment, the magnetic beads that comprise biotinylated capture probes hybridized to sequences amplified by the limited-cycle PCR are immobilized to one or more surfaces of a flow cell using a method of the disclosure.

In some embodiments, linear amplification on the beads and/or amplification of polynucleotides seeded on a flow cell surface can be performed using kinetic exclusion amplification (KEA), also referred to as exclusion amplification (ExAmp). A kinetic exclusion amplification reaction includes components that facilitate formation of select amplified products (e.g., strands released from beads). An example of ExAmp component is a recombinase. Recombinase can facilitate select amplified product formation by allowing repeated invasion/extension. More specifically, recombinase can facilitate invasion of a target nucleic acid by the polymerase and extension of a primer (primer invasion) by the polymerase using the target nucleic acid as a template for amplified product formation. The process can occur more rapidly than standard PCR since a denaturation cycle (e.g., via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590.

Helicase, is another example of a component of a kinetic exclusion amplification reaction that facilitates select amplified product formation, and in some cases, increases the rate of amplified product formation. The process can occur more rapidly than standard PCR since a denaturation cycle (e.g., via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, MA). Further, examples of useful formulations that include a helicase protein are described in U.S. Pat. Nos. 7,399,590 and 7,829,284. An origin binding protein, is yet another example of a component that can be included in an ExAmp reaction to facilitate amplified linear product formation. The beads can be removed from the flow cell prior to, or after the ExAmp driven polynucleotide release step.

Various flow cell devices can be used to carry out the methods of the disclosure, including flow cell devices made by Illumina, Inc. (e.g., HiSeq devices, NovaSeq devices, MiSeq devices, and NextSeq devices); flow cell devices made by F. Hoffmann-La Roche Ltd. (e.g., GS FLX devices, and GS Junior devices); and flow cell devices made by Life Sciences (e.g., SOLiD/Ion Torrent devices). In a particular embodiment, the flow cell device used to carry out a method of the disclosure is a flow cell device made by Illumina Inc.

In some embodiments, an exclusion amplification reaction can be used to amplify seeded polynucleotides on a flow cell surface. The exclusion amplification reaction proceeds until a sufficient number of amplicons are generated to fill the capacity of the respective amplification site, e.g., a well of a patterned flow cell. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example, in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

In some embodiments, kinetic exclusion can occur when a process occurs at a sufficiently rapid rate to effectively exclude another event or process from occurring. Take for example the making of a nucleic acid array on a flow cell surface where sites on the flow cell are randomly seeded with target nucleic acids from beads using the methods of the disclosure and copies of the target nucleic acid are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of US Application Pub. No. 2013/0338042.

Kinetic exclusion can exploit a relatively slow rate for initiating amplification (e.g., a slow rate of making a first copy of a target nucleic acid) vs. a relatively rapid rate for making subsequent copies of the target nucleic acid (or of the first copy of the target nucleic acid). In the example of the previous paragraph, kinetic exclusion occurs due to the relatively slow rate of target nucleic acid seeding (e.g., relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (e.g., delayed or slow activation) vs. the relatively rapid rate at which subsequent copies are made to fill the site. In this example, an individual site or well may have been seeded with several different target nucleic acids (e.g., several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site or well will rapidly fill to capacity with its copies, thereby preventing copies of a second target nucleic acid from being made at the site.

In some patterned flow cells, the patterned flow cells comprise wells that have size dimensions (e.g., diameter) that are selected in a range which favor kinetic exclusion amplification (KEA) and the formation of monoclonal populations of target-specific polynucleotides within a well. Kinetic exclusion amplification of nucleic acid libraries is described, e.g., in U.S. Patent Publication No. 2013/0338042. For example, the well size (e.g., diameter) can be varied between about 30 nm and about 1 μm, between about 50 nm and about 800 nm, between about 70 nm and about 600 nm, or between 100 nm and about 400 nm. In some embodiments, the well has a diameter of about 400 nm. In some embodiments, the well has a diameter of less than about 1 μm. Exemplary patterned flow cells include Illumina® HiSeq-X10 patterned flow cells.

In a further embodiment, the disclosure provides a method to increase the seeding efficiency of a patterned flow cell by performing on-flow cell linear amplification to copy polynucleotides captured on the flow cell surface and then performing "shallow layer liquid" denaturing and seeding to force the polynucleotide copy to be re-seeded in the nearby area. Examples of denaturants that can be used with such processes include, but are not limited to, use of heat, sodium hydroxide treatment, a high salt concentration, formamide, guanidine, sodium salicylate, dimethyl sulfoxide, propylene glycol and urea.

For the on-flow cell linear amplification step, any number of amplification techniques maybe used, including ExAmp as already discussed herein. Alternatively, AMS1 first extension can be used to generate double stranded DNA on the flow cell surface (one copied anchor strand with the original strand). For the "shallow layer liquid" denaturing step, a hybridization buffer which comprises a chemical denaturant (e.g., formamide) can be used, e.g., HT1 from Illumina™. A hybridization buffer generally includes a buffered salt solution, such as 5% SSPE or 5×SSC, and a small amount of a nonionic surfactant (e.g., 0.1% tween or 0.1% sodium dodecyl sulfate). The hybridization buffer can comprise a chemical denaturant, such as formamide or guanidine, at a percentage of 5%, 10%, 15%, 20%, 25%, 30%, 35%, 40%, 45%, 50% or a range that includes or is between any two of the foregoing percentages. The amount of hybridization used, should be sufficient to fluidly connect the wells of the patterned flow cell. After reseeding the polynucleotides, bridge amplification can then be used to form clusters on the surface of the patterned flow cell for further processes, such as sequencing.

For use in flow cell applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more bead-linked transposomes and reagents, e.g., soluble primer(s), ExAmp, buffers, etc. used to carry out the methods described herein. The container(s) optionally have a sterile access port (for example the container can be an intravenous solution bag or a vial having a stopper pierceable by a hypodermic injection needle). Such kits optionally comprise reagents with an identifying description or label or instructions relating to its use in the methods described herein.

A kit will typically comprise one or more additional containers, each with one or more of various materials (such as additional reagents, optionally in concentrated form, and/or devices) desirable from a commercial and user standpoint for use of bead-linked transposomes described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific flow cell application. The label can also indicate directions for use of the contents, such as in the methods described herein.

EXAMPLES

Figure 7A:
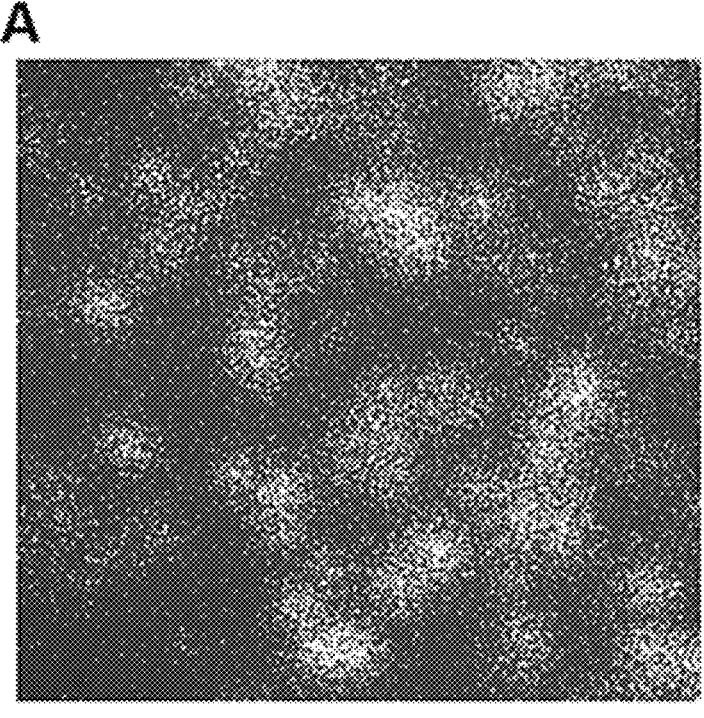
FIG. 7A-B presents the results of linear amplification on a well of a flow cell. (A) Clusters formed using standard seeding protocols. (B) Clusters formed using the linear amplification protocol described herein.
Figure 7B:
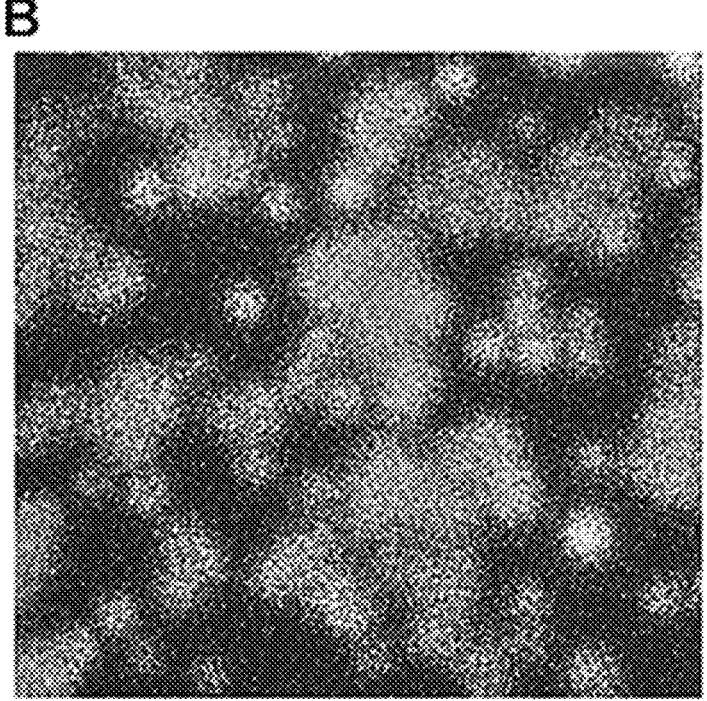

Evaluating the performance of on-flow cell linearization amplification methods. To check the performance of on-flow cell linearization amplification methods, the workflow was tested on a Miseq flow cell to plot out all the seeded/re-seeded DNA library molecules. FIG. 7A is the cluster cloud from the standard workflow (no shallow layer denaturing/re-seeding), and FIG. 7B is the clusters from same batch of the beads with shallow layer liquid denaturing/reseeding. The clusters in FIG. 7B are apparently more than that in FIG. 7A, showing the on-flow cell linear amplification workflow does successfully re-seed the original DNA library molecules to enable maximizing the sequencing info.

Checking the duplicates copy numbers to confirm the performance of on-flow cell linear amplification: Generation of long DNA fragment islands from the cluster cloud was also evaluated using the on-flow cell linear amplification workflow. Up to 4 copies of the duplicates (both strands of Y-adaptor library get doubled by shallow layer re-seeding) were observed. While with standard workflow, only up to two copies of duplicates (both strands of Y-adaptor library) were observed.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A method for seeding a flow cell with polynucleotide(s) released from a bead, comprising:
   (i) annealing a first primer to polynucleotide strands bound to a bead, wherein the 5' ends of the polynucleotide strands are bound to the bead using a first attachment agent, wherein the polynucleotide strands comprise adaptors that contain a sequence that is complementary to the sequence of the first primer, and wherein the first primer is in solution;
   (ii) extending from the first primer using a polymerase to form a double stranded polynucleotide product;
   (iii) carrying out primer invasion of the double stranded polynucleotide product by using additional amounts of the first primer and a recombinase;
   (iv) displacing and releasing from the bead a strand of the double stranded polynucleotide product of step (ii) by extending from the additional first primer in step (iii) using a polymerase;
   (v) seeding a flow cell by attaching the strand released in step (iv) to the surface of a flow cell using a second attachment agents; and
   optionally, repeating steps (iii) to (v) multiple times.

2. The method of claim 1, wherein the bead is comprised of a polymeric material, a silica material, a zirconia material, or a superparamagnetic material.

3. The method of claim 1, wherein the bead is functionalized with a coating or layer selected from biotin; streptavidin; amine groups; carboxyl groups; epoxy groups; tosyl groups; an antibody or an antigen; a polyhistidine tag or a carrier comprising a metal ion; and a receptor or a ligand.

4. The method of claim 1, wherein the beads are immobilized on one or more surfaces of the flow cell using an attachment agent.

5. The method of claim 4, wherein the attachment agent is a biotin/streptavidin linkage or base pairing between two complementary sequences.

6. The method of claim 1, wherein the polynucleotide strands bound to the bead comprise (i) genomic DNA, (ii) long template DNA; or (iii) DNA from a sample.

7. The method of claim 6, wherein the sample is a urine, blood, saliva, tissue, serum, plasma, sputum, bile, fecal, hair, skin, and/or primary cell sample.

8. The method of claim 1, wherein the polynucleotide strands are tagmented and bound to the bead by use of a transposome linked to the beads.

9. The method of claim 8, wherein the transposome linked to the beads comprises transposase Tn5, or a mutant or variant thereof.

10. The method of claim 1, wherein the polynucleotide strands comprise a first portion of sequence that was bound to the bead by first attachment agents and a second portion of sequence that was tagmented and ligated to the first portion of sequence by use of a transposomes linked to the bead and a ligase.

11. The method of claim 10, wherein the transposome linked to the beads comprises transposase Tn5, or a mutant or variant thereof.

12. The method of claim 10, wherein the first portion of the sequence comprises one or more barcode or index sequences, one or more universal primer sequences, and/or a mosaic end sequence.

13. The method of claim 12, wherein the first portion of the sequence comprises one or more barcode or index sequences, one or more universal primer sequences, and a mosaic end sequence, and wherein the mosaic end sequence is located at the 3' end of the first portion of the sequence.

14. The method of claim 10, wherein the adaptors comprise a first sequence that is complementary and can hybridize with the first portion of the sequence of the polynucleotide strands, and wherein the adaptors comprise a second sequence that is not complementary and cannot hybridize with the first portion of the sequence of the polynucleotide strands.

15. The method of claim 14, wherein the second sequence of the adaptors comprises a sequence that is complementary to the sequence of the first primer.

16. The method of claim 10, wherein the second portion of sequence of the polynucleotide strands comprises (i) gDNA, (ii) long template DNA, or (iii) DNA from a sample.

17. The method of claim 16, wherein the sample is a urine, blood, saliva, tissue, serum, plasma, sputum, bile, fecal, hair, skin, and/or primary cell sample.

18. The method of claim 1, wherein the first attachment agent and second attachment agent is selected from a biotin/streptavidin linkage, a covalent bond, base pairing between two complementary sequences, an antibody binding an antigen, an antibody binding another antibody, a polyhistidine tag binding a carrier comprising a metal ion, and a receptor binding a ligand.

19. The method of claim 18, wherein the first attachment agent is a biotin/streptavidin or avidin linkage, and wherein the second attachment agent is base pairing between two complementary sequences.

20. The method of claim 19, wherein the polynucleotide strands comprise biotin residues at the 5' ends, and the bead comprises streptavidin residues.

* * * * *

```
                          SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Universal capture sequence primer P5

<400> SEQUENCE: 1
aatgatacgg cgaccaccga                                              20

<210> SEQ ID NO 2
<211> LENGTH: 21
<212> TYPE: DNA
<213> ORGANISM: Artificial Sequence
<220> FEATURE:
<223> OTHER INFORMATION: Universal capture sequence primer P7

<400> SEQUENCE: 2
caagcagaag acggcatacg a                                            21

<210> SEQ ID NO 3
<211> LENGTH: 20
<212> TYPE: DNA
<213> ORGANISM: Artificial Sequence
<220> FEATURE:
<223> OTHER INFORMATION: Universal capture sequence primer anti-P5

<400> SEQUENCE: 3
tcggtggtcg ccgtatcatt                                              20

<210> SEQ ID NO 4
<211> LENGTH: 21
<212> TYPE: DNA
<213> ORGANISM: Artificial Sequence
<220> FEATURE:
<223> OTHER INFORMATION: Universal capture sequence primer anti-P7

<400> SEQUENCE: 4
tcgtatgccg tcttctgctt g                                            21

<210> SEQ ID NO 5
<211> LENGTH: 33
```

-continued

```
<212> TYPE: DNA
<213> ORGANISM: Artificial Sequence
<220> FEATURE:
<223> OTHER INFORMATION: SBS3 primer

<400> SEQUENCE: 5
acactctttc cctacacgac gctcttccga tct                        33

<210> SEQ ID NO 6
<211> LENGTH: 37
<212> TYPE: DNA
<213> ORGANISM: Artificial Sequence
<220> FEATURE:
<223> OTHER INFORMATION: SBS8 primer

<400> SEQUENCE: 6
cggtctcggc attcctgctg aaccgctctt ccgatct                    37

<210> SEQ ID NO 7
<211> LENGTH: 33
<212> TYPE: DNA
<213> ORGANISM: Artificial Sequence
<220> FEATURE:
<223> OTHER INFORMATION: anti-SBS3 primer

<400> SEQUENCE: 7
agatcggaag agcgtcgtgt agggaaagag tgt                        33

<210> SEQ ID NO 8
<211> LENGTH: 37
<212> TYPE: DNA
<213> ORGANISM: Artificial Sequence
<220> FEATURE:
<223> OTHER INFORMATION: anti-SBS8 primer

<400> SEQUENCE: 8
agatcggaag agcggttcag caggaatgcc gagaccg                    37
```